United States Patent
Bergson

(10) Patent No.: US 7,220,851 B2
(45) Date of Patent: May 22, 2007

(54) NUCLEIC ACID ENCODING CALCYON, A D-1 LIKE DOPAMINE RECEPTOR ACTIVITY MODIFYING PROTEIN

(75) Inventor: Clare Bergson, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 702 days.

(21) Appl. No.: 10/237,523

(22) Filed: Sep. 9, 2002

(65) Prior Publication Data

US 2003/0073818 A1    Apr. 17, 2003

Related U.S. Application Data

(62) Division of application No. 09/416,509, filed on Oct. 8, 1999, now Pat. No. 6,469,141.

(60) Provisional application No. 60/130,609, filed on Apr. 22, 1999, provisional application No. 60/103,786, filed on Oct. 9, 1998.

(51) Int. Cl.
*C07H 21/04* (2006.01)
*C12N 1/21* (2006.01)
*C12N 15/12* (2006.01)
*C12P 21/02* (2006.01)

(52) U.S. Cl. ............... 536/23.5; 435/69.1; 435/253.3; 530/350; 536/23.1; 536/24.31; 536/24.33

(58) Field of Classification Search ............... None
See application file for complete search history.

(56) References Cited

U.S. PATENT DOCUMENTS 6,020,143 A * 2/2000 St. George-Hyslop et al. .. 435/7.1

FOREIGN PATENT DOCUMENTS

WO    WO 99/58642 A2    11/1999

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problems and Tertiary Structure Prediction. Birkhauser:Boston, pp. 492-495.*
Mikayama et al. (1993). Molecular cloning and functional expression of a cDNA encoding glycosylation-inhibiting factor. Proc. Natl. Acad. Sci. USA. 90:10056-10060.*
Spiegel, A.M. (1995), Defects in G protein-coupled signal transduction in human disease. Annual Rev. Physiol. 58:143-170.*
Pauwels et al. (1998). Review: amino acid domains involved in constitutive activation of G-protein-coupled receptors. Molec. Neurobiol. 17(1-3): 109-135.*
Skolnick et al. (2000). From genes to protein structure and function: novel applications of computational approaches in the genomic era. Trends in Biotech. 18(1):34-39.*
Bork, A. (2000). Powers and pitfalls in sequence analysis: the 70% hurdle. Genome Res. 10:398-400.*
Doerks et al. (1998). Proteins annotation: detective work for function prediction. Trends in Genetics. 14(6):248-250.*
Smith et al. (1997). The challenges of genome sequence annotation or The devil is in the details. Nature Biotech. 15:1222-1223.*
Brenner, S.E. (1999). Errors in genome function. Trends in Genetics. 15(4):132-133.*
Bork et al. (1996). Go hunting in sequence databases but watch out for the traps. Trends in Genetics. 12(10):425-427.*
Lezcano et al. (2000). Dual signaling regulated by calcyon, a D1 dopamine receptor interacting protein. Science. 287:1660-1664.*
Tiberi et al. (1994). High agonist-independent activity is a distinguishing feature of the dopamine D1B receptor subtype. The Journal of Biological Chemistry. 269(45):27925-27931.*
Allen, J. B. et al., Finding prospective partners in the library: The two-hybrid system and phage display find a match, *TIBS*, 20:511-516 (1995).
Artalejo, et al., Activation of facilitation calcium channels in chromaffin cells by D2 dopamine receptors through a cAMPo/ protein kinase A- dependent mechanism, *Nature*, 348(6298):239-242 (1990).

(Continued)

*Primary Examiner*—Christine J. Saoud
*Assistant Examiner*—Jon M. Lockard
(74) *Attorney, Agent, or Firm*—Kilpatrick Stockton LLP

(57) ABSTRACT

A number of cDNA clones whose products may interact with D1 receptors in vivo were identified. One of the clones, P24, was characterized further. P24 is localized in dendrites and spines of pyramidal cells in PFC. The extent of overlap between P24 expressing and D1 receptor expressing pyramidal cells appeared to be 100%. In contrast, only a limited number D1 receptor antibody labeled neurons in caudate expressed P24. P24 lowers the threshold of D1 receptor response to dopamine (DA) by an order of magnitude. Sequence similarity suggests P24 is a diverged member of the RAMP family. The P24 protein is therefore referred to as a D1 DA RAMP, calcyon. The isolated protein and nucleotide molecule encoding the protein, as well as primers for the nucleotide, are described. The protein and compounds modifying DA binding to the receptor or calcium release which is mediated by the Calcyon, are useful in research studies, drug screening, and therapeutically.

9 Claims, 6 Drawing Sheets

OTHER PUBLICATIONS

Bergson, C., et al., Characterization of subtype-specific antibodies to the human D5 dopamine receptor: studies in primate brain and transfected mammalian cells, *Proc. Natl. Acad. Sci. USA*, 92:3468-3472 (1995).

Bergson, et al., Regional, celluylar, and subcellular variations in the distribution of D1 and D5 dopamine receptors in primate brain, *J. Neurosci.*, 15(12):7821-7836 (1995).

Blin, et al., Mapping of single amino acid residues required for selective activation of Gq/11 by the m3 muscarinic acetylcholine receptor, *J. Biol. Chem.*, 270(30):17741-17748 (1995).

Bluml, et al., Identification of an intracellular tyrosine residue critical for muscarinic receptor-mediated stimulation of phosphatidylinositol hydrolysis, *J. Biol. Chem.*, 269(1):402-405 (1994).

Boehm, et al., Developmentally regulated and tissue specific expression of mRNAs encoding the two alternative forms of the LIM domain oncogene rhombotin: evidence for thymus expression, *Oncogene*, 6(5):695-703 (1991).

Cameron & Williams, Dopamine D1 receptors facility transmitter releast, *Nature*, 366(6453):344-347 (1993).

Canfield, V. A. and Levenson, R., Transmembrance organization of the Na,K-ATPase determined by epitope addition, *Biochemistry*, 32:13782-13786 (1993).

Carlock, L., et al., GenEMBL Sequence M98530, The identification of a neuron specific gene that maps adjacent to the Huntington's Disease marker D4S10 that shows homology to protein phosphatase inhibitors, (Mouse 19 kDa protein gene, complete coding sequence).

Casey, Protein lipidation in cell signaling, *Science*, 268(5208):221-225 (1995).

Cepeda, et al., Differential modulation by dopamine of responses evoked by excitatory amino acids in human cortex, *Synapse*, 11:330-341 (1992).

Cepeda, et al., Neuromodulatory actions of dopamine in the neostriatum are dependent upon the excitatory amino acid receptor subtypes activiated, *Proc. Natl. Acad. SCi. USA*, 90(20):9576-9580 (1993).

Chen, et al., One-step transformation of yeast in stationary phase, *Curr. Genet.*, 21(1):83-84 (1992).

Coghlan, et al., Association of protein kinase A and protein phosphatase 2B with a common anchoring protein, *Science*, 267(5194):108-111 (1995).

Dolph, et al., Arrestin function in inactivation of G protein-coupled receptor rodopsin in vivo, *Science*, 260:1910-1916 (1995).

Durfee, et al., The retinoblastoma protein associates with protein phosphatase type 1 catalytic subunit, *Genes Dev.*, 7(4):555-569 (1993).

Ellison & See, Rats administered chronic neuroleptics develop oral movements which are similar in form to those in humans with tardive dyskinesia, *Psychopharmacology (Berl).*, 98(4):564-566 (1989).

Eubanks, et al., Cloning of a novel neuronal dendritic protein that interacts with D1 dopamine receptors, *Society for Neuroscience Abstracts*, 24:1359 (1998).

Faux & Scott, Molecular glue: kinase anchoring and scaffold proteins, *Cell*, 85(1):9-12 (1996).

Ferguson, et al., Role of beta-arrestin in mediating agonist-promoted G protein-coupled receptor internalization, *Science*, 271(5247):363-366 (1996).

Fields & Song, a novel genetic system to detect protein-protein interaction, *Nature*, 340(6230):245-246 (1989).

Formosa, et al., Using protein affinity chromatography to probe structure of protein machines, *Methods in Enzymology*, 208:24-45 (1991).

Froehner, et al., The submembrane machinery for nicotinic acetylcholine receptor clustering, *J. Cell. Biol.*, 114(1):1-7 (1991).

Fujiwara, T., GenEMBL Sequence D79577, EST HUM282E10B.

Gautam, et al., Failure of postsynaptic specialization to develop at neuromuscular junctions of rapsyn-deficient mice, *Nature*, 377(6546):232-236 (1995).

Gill, The enigma of LIM domains, *Structure*, 3(12):1285-1289 (1995).

Gilmore, et al., Full dopamine D1 agonists in human caudate: Biochemical properties and therapeutic implications, *Nueropharmacology*, 34(5):481-488 (1995).

Gingrich & Caron, Recent advances in the molecular biology of dopamine receptors, *Annu. Rev. Neurosci.*, 16:299-321 (1993).

Glaser, et al., Myristoylated alanine-rich C kinase substrate (MARCKS) produces reversible inhibition of phospholipase C by sequestering phosphatidylinositol 4,5-bishosphate in lateral domains, *J. Biol. Chem.*, 271(42):26187-26193 (1996).

Grandy, et al., Multiple Human $D_5$ dopamine receptor genes: A functional receptor and two pseudogenes, *Proc. Natl. Acad. Sci. USA*, 88:9175-9179 (1991).

Grynkiewicz, et al., A new generation of CA2+ indicators with greatly improved fluroscence properties, *J. Biol. Chem.*, 260(6):3440-3450 (1985).

Hamm, The many faces of G protein signaling, *J. Biol. Chem.*, 273(2):669-672 (1998).

Harris & Kater, Dendritic spines: Cellular specializations imparting both stability and flexibility to synaptic function, *Annu. Rev. Neurosci.*, 17:341-371 (1994).

Huang & Kandel, D1/D5 receptor agonists induce a proten synthesis-dependent late potentiation in the CA1 region of the hippocampus, *Proc. Natl. Acad. Sci. USA*, 92(7):2446-2450 (1995).

Huntley, et al., Localization of multiple dopamine receptor subtype mRNAs in human and monkey motor cortex and striatum, *Mol. Brain Res.*, 15(3-4):181-188 (1992).

Jarvie, et al., Dopamine D1A and D1B receptors. Dopamine receptor heterogeneity, *Dopamine Receptors and Transporters: Pharmacology Structure and Function*, pp. 133-150.

Ji, et al., G protein-coupled receptors. 1. Diversity of receptor-ligand interactions, *J. Biol. Chem.*, 273(28):17299-17302 (1998).

Jones, GABAergic neurons and their role in cortical plasticity in primates, *Cereb. Cortex.*, 3(5):361-372 (1993).

Kirsch & Betz, The postsynaptic localization of the glycine receptor-associated protein gephyrin is regulated by the cytoskelton, *J. Neurosci.*, 15(6):4148-4156 (1995).

Kirsch, et al., Gephryin antisense oligonucleotides prevent glycine receptor clustering in spinal neurons, *Nature*, 366(6457):745-748 (1993).

Klauck, et al., Coordination of three signaling enzymes by AKAP79, a mammalian scaffold protein, *Science*, 271(5255):1589-1592 (1996).

Konradi, et al., Amphetamine and dopamine-induced immediate early gene expression in striatal neurons depends on postsynaptic NMDA receptors and calcium, *J. Neurosci.*, 16(13):4231-4239 (1996).

Kornau, et al., Domain interaction between NMDA receptor subunits and the postsynaptic density protein PSD-95, *Science*, 269(5231):1737-1740 (1995).

Kyte & Doolittle, A simple method for displaying the hydropathic character of a protein, *J. Mol. Biol.*, 157:105-132 (1982).

Laemmli, Cleavage of structural proteins during the assembly of the head of bacteriophage T4, *Nature*, 227(259):680-685 (1970).

Laurier, et al., Heterogeneous tissue-specific transcription of dopamine receptor subtype messenger RNA in rat brain, *Mol. Brain Res.*, 25(3-4):344-350 (1994).

Lefkowitz, G protein-coupled receptors. III. New roles for receptor kinases and beta-arrestins in receptor signaling and desensitization, *J. Biol. Chem.*, 273(30):18677-18680 (1998).

Levey, et al., Localization of D1 and D2 dopamine receptors in brain with subtype-specific antibodies, *Proc. Natl. Sci. USA*, 90(19):8861-8865 (1993).

Levine, et al., Modulatory actions of dopamine on NMDA receptor-mediated responses are reduced in D1A-deficient mutant mice, *J. Neurosci.*, 16(18):5870-5882 (1996).

Li, et al., A huntingtin-associated protein enriched in brain with implications for pathology, *Nature*, 378(6555):398-402 (1995).

Lin, et al., Characterization of cloned human dopamine d1 receptor-mediated calcium release in 293 cells, *Molecular Pharmacology*, 47:131-139 (1995).

Marra, M., GenEMBL Sequence AA060454, EST mj69c06.r1, Mouse cyclohydrolase I mRNA.

McLatchie, et al., RAMPs regulate the transport and ligand specificity of the calcitonin-receptor-like receptor, *Nature*, 393(6683):333-339 (1998).

Mochly-Rosen, D., Localization of protein kinases by anchoring proteins: A theme in signal transduction, *Science*, 268(5208):247-251 (1995).

Mrzljak et al., Association of m1 and m2 muscarinic receptor proteins with asymmetric synapses in the primate cerebral cortex: morphological evidence for cholinergic modulation of excitatory neurotransmission, *Proc. Natl. Acad. Sci. USA*, 90(11):5194-5198 (1993).

Mrzljak, et al., Localization of dopamine D4 receptors in GABAergic neurons of the primate brain, *Nature*, 381:245-248 (1996).

Oancea, et al., Protein kinase C as a molecular machine for decoding calcium and diacylglycerol signals, *Cells*, 95(3):307-318 (1998).

O'Dowd, et al., Dopamine Receptors, *Handbook of Receptors and Channels*, pp. 95-123, CRC Press, Inc. (1994).

Pepperl, D. J., et al., Cloning of proteins interacting with the D2A dopamine receptor third intracellular loop, *Society for Neuroscience*, vol. 21, Abstract 253.11 (1995).

Phillips, et al., ACh receptor-rich membrane domains organized in fibroblasts by recombinant 43-kildalton protein, *Science*, 251(4993):568-570 (1991).

Richards, et al., The Enzymes, vol. 4 (Boyer, P.D., ed.) *Academic Press*, NY (1971).

Rothman, Mechanisms of intracellular protein transport, *Nature*, 372:55-63 (1994).

Sabéran-Djoneidi, et al., A 19-kDa protein belonging to a new family is expressed in the Golgi apparatus of neural cells, *J. Biol. Chem.*, 270(4):1888-1893 (1995).

Sawaguchi & Goldman-Rakic, D1 dopamine receptors in prefrontal cortex: involvement in working memory, *Science*, 251(4996):947-950 (1991).

Schokett, et al., A modified tetracycline-regulated system provides autoregulatory, inducible gene expression in cultured cells and transgenic mice, *Proc. Natl. Acad. Sci, USA*, 92(14):6522-6526 (1995).

Schwager, Arnold, G.J., et al., GenEMBL Sequence F13805.

Smiley, et al., D1 dopamine receptor immunoreactivity in human and monkey cerebral cortex: predominant and extrasynaptic localization in dendritic spines, *Proc. Natl. Acad., Sci. USA*, 91(12):5720-5724 (1994).

Smith, et al., Synaptic relationships between dopaminerigic afferents and cortical of thalamic input in the sensorimotor territory of the striatum in monkey, *J. Comp. Neurol.*, 344(1):1-19 (1994).

Spooren, et al., Dopamine D1 receptors in the sub-commissural part of the globus pallidus and their role in orofacial dyskinesia in cats, *Eur. J. Pharmacol.*, 204(2):217-222 (1991).

Steiner & Gerfen, Dynorphin opioid inhibition of cocaine-induced, D1 dopamine receptor-mediated immediate-early gene expression in the striatum, *J. Comp. Neurol.*, 353(2):200-212 (1995).

Strausberg, TM71B06.x1 *Homo sapiens* cDNA clone (EST), *Database EMBL* A1480012 (1999).

Surmeier, et al., Modulation of calcium currents by a D1 dopaminergic protein kinase/phosphatase cascade in rat neostriatal neurons, *Neuron.*, 14(2):385-397 (1995).

Sutcliffe, et al., Identifying the protein products of brain-specific genes with antibodies to chemically synthesized peptides, *Cell*, 33(3):671-682 (1983).

Taber & Fibiger, Electrical sitmulation of the prefrontal cortex increases dopamine release in the nucleus accumbens of the rat: modulation by metabotropic glutamate receptors, *J. Neurosci.*, 15(5):3896-3904 (1995).

Towbin, et al., Electrophoretic transfer of proteins from polyacrylamide gels to nitrocellulose sheets: procedure and some applications, *Proc. Natl. Acad. Sci. USA*, 76(9):4350-4354 (1979).

Voet, D. and Voet, J.G., Biochemistry $2^{nd}$ Edition, *John Wiley & Sons, Inc.*, NY, p. 125 (1995).

Wang, et al., Evidence for the coupling of Gq protein to D1-like dopamine sites in rat striatum: possible role in dopamine-mediated inositol phosphate formation, *Mol. Pharmacol.*, 48(6):988-994 (1995).

Wang, et al., Ribozyme-mediated suppression of the G protein gamma7 subunit suggests a role in hormone regulation of adenylylcyclase activity, *J. Biol. Chem.*, 272(41):26040-26048 (1997).

Wang, et al., The full D1 dopamine receptor agonist SKF-82958 induces neuropeptide mRNA in the normosensitive striatum of rats: regulation of D1/D2 interactions by muscarinic receptors, *J. Pharmacol. Exp. Ther.*, 281(2):972-982 (1997).

Williams, et al., Modulation of memory fields by dopamine D1 receptors in prefrontal cortex, *Nature*, 376(6541):572-575 (1995).

Wilson, R. K., GenEMBL Sequence N70566.

Wojcikiewicz, et al., Phosphorylation of inositol 1,4,5-trisphosphate receptors by cAMP-dependent protein kinase. Type I, II, and III receptors and differentially susceptible to phosphorylation and are phosphorylated in intact cells, *J. Biol. Chem.*, 273(10):5670-5677 (1998).

Yu, et al. Differential regulation of renal phospholipase C isoforms by catecholamines, *J. Clin. Invest.*, 95(1):304-308 (1995).

Yung, K. K. L., Immunocytochemical localization of D1 and D2 Dopamine Receptors in the basal ganglia of the rat: Light and electron microscopy, *Neuroscience*, vol. 65, No. 3, pp. 709-730 (1995).

Zhang, et al., The fragile X mental retardation syndrome protein interacts with novel homologs FXR1 and FXR2, *EMBO J.*, 14(21):5348-5366 (1995).

Zhou, et al., Cloning and expression of human and rat D1 dopamine receptors, *Nature*, 347(6288):76-80 (1990).

International Preliminary Examination Report mailing dated Feb. 18, 2000 for PCT/US99/23565, International Filing Date Aug. 10, 1999.

Mikayama et al., Molecular cloning and functional expression of a cDNA encoding glycosylation-inhibiting factor, *Proc. Natl. Acad. Sci. USA*, 90:10056-10060 (1993).

Rieger et al., Glossary of Genetics & Cytogenetics, $4^{th}$ Ed., *Springer-Verlag*, 16-19 (1976).

Xiao, J. et al., "Calcyon, a Novel Partner of Clathrin Light Chain, Stimulates Clathrin-Mediated Endocytosis," Journal of Biological Chemistry, vol. 281, No. 22, pp. 15182-15193, 2006.

* cited by examiner

```
-115 GAATTCGCGGCCGCGTCGACCGCATCCTCCGCATCCACATCCGCATCGTCGTCCTC
     CCCGACCGCGTCCTGCAGCAGCTGCCAGTGGAGCCGCCTGACAAGGGACTGCCATCCACC

MetValLysLeuGlyCysSerPheSerGlyLysProGlyLysAspProGlyAspGlnAsp    20
     ATGGTGAAGCTGGGCTGCAGCTTCTCTGGGAAGCCAGGTAAAGACCCTGGGGACCAGGAT    60

GlyAlaAlaMetAspSerValProLeuIleSerProLeuAspIleSerGlnLeuGlnPro    40
     GGGGCTGCCATGGACAGTGTGCCTCTGATCAGCCCCTTGGACATCAGCCAGCTCCAGCCG   120

ProLeuProAspGlnValValIleLysThrGlnThrGluTyrGlnLeuSerSerProAsp    60
     CCACTCCCTGACCAGGTGGTCATCAAGACACAGACAGAATACCAGCTGTCCTCCCCAGAC   180
                                    *
     GlnGlnAsnPheProAspLeuGluGlyGlnArgLeuAsnCysSerHisProGluGluGly    80
     CAGCAGAATTTCCCTGACCTGGAGGGCCAGAGGCTGAACTGCAGCCACCCAGAGGAAGGG   240

ArgArgLeuProThrAlaArgMetIleAlaPheAlaMetAlaLeuLeuGlyCysValLeu   100
     CGCAGGCTGCCCACCGCACGGATGATCGCCTTCGCCATGGCGCTACTGGGCTGCGTGCTG   300

IleMetTyrLysAlaIleTrpTyrAspGlnPheThrCysProAspGlyPheLeuLeuArg   120
     ATCATGTACAAGGCCATCTGGTACGACCAGTTCACCTGCCCCGACGGCTTCCTGCTGCGG   360

HisLysIleCysThrProLeuThrLeuGluMetTyrTyrThrGluMetAspProGluArg   140
     CACAAGATCTGCACGCCGCTGACCCTGGAGATGTACTACACGGAGATGGACCCCGAGCGC   420

HisArgSerIleLeuAlaAlaIleGlyAlaTyrProLeuSerArgLysHisGlyThrGlu   160
     CACCGCAGCATCCTGGCGGCCATCGGGGCCTACCCGCTGAGCCGCAAGCACGGCACGGAG   480

ThrProAlaAlaTrpGlyAspGlyTyrArgAlaAlaLysGluGluArgLysGlyProThr   180
     ACGCCGGCGGCCTGGGGGGACGGCTACCGCGCAGCCAAGGAGGAGCGCAAGGGGCCCACC   540

GlnAlaGlyAlaAlaAlaAlaAlaThrGluProProGlyLysProSerAlaLysAlaGlu   200
     CAGGCTGGGGCGGCGGCGGCGGCCACCGAACCCCCCGGGAAGCCGTCGGCCAAGGCGGAG   600

LysGluAlaAlaArgLysAlaAlaGlySerAlaAlaProProProAlaGlnEnd         217
     AAGGAGGCGGCGCGGAAGGCGGCCGGGAGCGCGGCGCCCCCGCCCGCGCAGTGACGTCTC   660
     CAGCCCCGCAGCCCGGCCCGGGCGTCCTCCGCCAGCTCCTGTGACCAGCGCGTCTCCCGA
     TGCTCTCCGCCGTGTTCGTGTCCCCAGGCGCCCTCGCTGCAGCCCCGCCCCCGTGGGTCT
     CTGACTCTGTCGCTTTTCTCTAAGTAAAGATTTCACGTCC  820
```

*Fig. 1*

| | | | | | | | | |
|---|---|---|---|---|---|---|---|---|
| Calcyon | 1 | MVKLGCSFSG | KPGKDPGDQD | GAAMDSVPLI | SPLDISQLQP | PLPDQVVIKT | QTEYQ | |
| P19 | 1 | MVKLNSNPGE | KGAKPPSVED | G..FQTVPLI | TPLEVNHLQL | AAPEKVIVKT | RTEYQ | |
| P21 | 1 | MVKLGNNFAE | KGTKQPLLED | G..FDTIPLM | TPLDVNQLQF | PPPDKVVVKT | KTEYE | |
| | | | | | | | | |
| Calcyon | 56 | LSSPD | QQNFPDLEGQ | RLNCSHPE.. | EG..RRLPTA | RMIAFAMALL | GCV..LIMYK | |
| P19 | 54 | ...PE | QRNKGKFRVP | KIAEFTV... | .........T | ILVSLALAFL | ACIVFLVVYK | |
| P21 | 54 | ...PD | .RKKGKARPP | QIAEFTVSIT | EGVTERFKVS | VLVLFALAFL | TCVVFLVVYK | |
| | | | | | | | | |
| Calcyon | 105 | AIWYDQFTCP | DGFLLRHKIC | TPLTLEMYYT | EMDPERHRSI | LAAIGAYPLS | RKHG | |
| P19 | 94 | AFTYDH.SCP | EGFVYKHKRC | IPASLDAYYS | SQDPSSRSRF | YTVISHYSVA | KQST | |
| P21 | 105 | VYKYDR.ACP | DGFVLKNTQC | IPEGLESYYA | EQDSSAREKF | YTVINHYNLA | KQSI | |
| | | | | | | | | |
| Calcyon | 159 | TETPAA | WGDCYRAAKE | ERKGPTQAGA | AAAATEPPGK | PSAKAEKEAA | RKAAGSAAP | |
| P19 | 147 | ARAGP | WLSAAAVIHE | P.KPPKTQGH | .......... | .......... | ......... | |
| P21 | 158 | TRSP | WMSVLSEEKL | S.EQETEAAE | KSA....... | .......... | ......... | |
| | | | | | | | | |
| Calcyon | 214 | P PAQ | | | | | | |
| P19 | | . ... | | | | | | |
| P21 | | . ... | | | | | | |

Fig. 2

NUCLEIC ACID ENCODING CALCYON, A D-1 LIKE DOPAMINE RECEPTOR ACTIVITY MODIFYING PROTEIN

CROSS REFERENCE TO RELATED APPLICATIONS

This application claims priority to U.S. patent application Ser. No. 60/103,786, filed Oct. 9, 1998 and U.S. patent application Ser. No. 60/130,609, filed Apr. 22, 1999. This application is a divisional of U.S. patent application Ser. No. 09/416,509, filed Oct. 8, 1999, now U.S. Pat. No. 6,469,141. U.S. patent application Ser. No. 60/103,786, filed Oct. 9, 1998, U.S. patent application Ser. No. 60/130,609, filed Apr. 22, 1999, and U.S. patent application Ser. No. 09/416,509, filed Oct. 8, 1999, are hereby incorporated herein by reference.

BACKGROUND OF THE INVENTION

This is in the general area of protein receptors, and more specifically relates to isolation and cloning of a D1-like receptor activity modifying protein (RAMP) which is a single transmembrane protein, designated P24, or calcyon, that interacts with a C-terminal intracellular segment of the hD1 DA receptor, and use thereof in screening for therapeutics and diagnostics.

The human D1 dopamine (DA) receptor displays micromolar affinity for the neuromodulator DA. Currently, the management of many psychiatric and movement disorders relies heavily on the inhibition or facilitation of DA at its receptors. Via DA receptors, DA and DA mimetic ligands, such as antipsychotic drugs, exert both short and long term changes in ion channel activity, protein kinase/phosphatase activities, and gene expression (Artalejo et al., *Nature* 348: 239–42 (1990); Steiner and Gerfen, *J. Comp. Neurol.* 353: 200–12 (1995); Surmeirer et al., *Neuron* 14:385–97(1995)). The design of most of these drugs has been based on a "D1" and "D2" DA receptor subtype paradigm. However, molecular cloning has led to the identification of five mammalian DA receptor subtypes (D1–D5) (reviewed in Gingrich and Caron, *Annu. Rev. Neurosci.* 16:299–321 (1993)). Individual subtypes have been further characterized as D1-like (D1 and D5) or D2-like (D2, D3 and D4) based on their selectivity for either classical "D1" or "D2" dopaminergic ligands. Thus, conceptualizations of how DA modulates the mesolimbic, mesocortical and nigrastriatal pathways through "D1" and "D2" receptors are inadequate given the added molecular complexity of the DA receptor system. The functional implications of these "new" "D1" and "D2" DA receptor subtypes for DA in regulating cognitive, motor and associative functions is currently unknown. However, their discovery presents new opportunities for obtaining a more precise understanding of the role of dopaminergic neurotransmission in these processes. In addition, a complete understanding of the cellular and molecular processes regulating the specific subtype functions is crucial for dealing with disorders like schizophrenia, Parkinson's disease, Tourette's syndrome, and drug addiction that appear to involve dysfunction in the DA system.

In brain, D1 receptors are most abundant in the caudate nucleus, where they are involved in the control of movement. D1 receptors are also found in prefrontal cortex (PFC) where they are required for working memory, a form of memory impaired in schizophrenia. In PFC, D1 receptors are present in pyramidal cell dendritic spines typically located several micrometers away from DA terminals.

Immunohistochemical analyses of the D1-like dopamine (DA) receptor subtypes, D1 and D5, shows that each receptor protein has a unique cellular and subcellular distribution within the mesocortical, mesolimbic, and nigrastriatal pathways. These results support the notion that each D1-like subtype serves a distinct function. However, the molecules that may mediate subtype-specific signal transduction differences in vivo have not yet been identified. In addition, details regarding the processes specifying the subcellular distribution of each receptor subtype are unclear. Without this molecular information, it is difficult to understand the physiologic requirements for multiple D1-like subtypes. Examination of well-characterized systems indicates that most processes in cells are mediated by protein complexes created by specific protein-protein interactions (Formosa et al., *In: Methods in Enzymology: Academic Press, Inc.* pp 24–45 (1991)).

As a group, the five mammalian DA receptor subtypes comprise a subfamily of the G-protein coupled receptor (GPCR) superfamily with predicted seven transmembrane topology. Similarities in genomic organization, sequence, and G-protein coupling suggest that the two DA receptor families evolved from prototypical D1 and D2 receptor genes via duplication and divergence (O'Dowd et al., In *Handbook of Receptors and Channels:* CRC Press, Inc., pp 95–123 (1994)). Although each of the D1-like and D2-like subtypes are presumed to serve distinct functions, subtype-specific signal transduction differences have not been identified in vivo. Without this functional information, it is difficult to understand the physiologic requirements for multiple D1-like and D2-like receptor subtypes. Using the D1 and D5 D1-like subtypes as a model, one can elucidate the physiologic basis for multiple DA receptor subtypes by defining molecular determinants of their functions. Information obtained from this research should lead to a more sophisticated understanding of the principles guiding the functional organization of dopaminergic pathways. Several classes of proteins that regulate GPCR's are known, yet none have been found to alter the sensitivity of D1 receptors in vivo.

There is ample pharmacological, electrophysiological and behavioral evidence to testify to the importance of D1-like receptors in cognitive and motor processes under normal or pathological conditions, including tardive dyskinesia (Ellison and See, *Pyschopharmacology* 98:564 (1989); Spooren et al., *Euro. J. Pharmacol.* 204:217 (1991)), Parkinson's Disease (Gilmore et al., *Neuropharmacology* 34:481–8 (1995)), working memory (Sawaguchi and Goldman-Rakic, *Science* 251:947–50 (1991)), and long term potentiation (Huang and Kandel, *Proc. Natl. Acad. Sci. USA* 92:2446–50 (1995)). However, whether the primary D1-like receptor involved is D1, or D5, or both, in each of these processes/behaviors is completely unclear because both subtypes have similar affinities for "D1" receptor agonists and antagonists. mRNA and protein localization studies in rodent and primate have provided the most revealing insights into the different functions of the D1 and D5 subtypes in vivo (Huntley et al., *Mol. Brain Res.* 15:181–8 (1992); Levey et al., *Proc. Natl. Acad. Sci. USA* 90:8861–5 (1993); Smiley et al., *Proc. Natl. Acad. Sci. USA* 91:5720–4 (1994); Laurier et al., *Mol. Brain Res.* 25:344–350 (1994); Bergson et al., *J. Neurosci.* 15:7821–36 (1995)). Although the D1 subtype is the most abundant DA receptor subtype, many aspects of the D5 subtype's localization in cerebral cortex and limbic nuclei suggest that it may support DA's actions in the higher cognitive, associative and affective processes uniquely associated with humans. In contrast, the most abundant expression of D1 receptors is detected in the basal ganglia nuclei which are primarily associated with movement.

Previous studies carried out with subtype-specific antibodies indicate that D1 and D5 receptor proteins are typically coexpressed in pyramidal neurons of monkey prefrontal cortex. However, initial electron microscopic studies suggest that D1 receptors are preferentially localized in spines of pyramidal neurons, and D5 receptors are mainly associated with their apical dendrites (Bergson et al., *J. Neurosci.* 15:7821–36 (1995)). As the synaptic input to spines is excitatory, and synaptic input to shafts is generally inhibitory (Jones, *Cerebral Cortex* 3:361–72 (1993); Harris and Kater, *Annu. Rev. Neurosci.* 17:341–71 (1994); Smith et al., *J. Comp. Neurol.* 344:1–19 (1994)), it seems reasonable to speculate that the two D1-like receptors may, in fact, be carrying out different functions. Their differential localization in pyramidal cell dendritic spines and shafts is consistent with the idea that D1 and D5 receptors initiate biochemical events that modulate excitatory or inhibitory synaptic transmission, respectively. This possibility has been supported by numerous electrophysiological studies (Cepeda et al., *Proc. Natl. Acad. Sci. USA* 90:9576–80 (1993); Cameron and Williams, *Nature* 366:344–7 (1993); Taber and Fibiger, *J. Neurosci.* 15:3896–904 (1995)). Indeed, a recent electrophysiological study demonstrated that DA's normal ability to potentiate responses to NMDA is blunted in D1 knockout mice (Levine et al., *J. Neurosci.* 16:5870–82 (1996)).

D1 and D5 receptors, like a number of other GPCRs expressed in brain, stimulate adenyl cyclase in the presence of agonist presumably via coupling to a Gs-like G-protein. However, knowledge of whether D1 or D5 subtypes elicit specific physiological responses in vivo is lacking. It is also unclear whether receptor-specific regulatory steps exist to modify D1 versus D5 receptor activation. This molecular information is critical for developing therapies that might inhibit or activate a D1 or D5 specific function.

It is an object of the present invention to provide reagents which can be used to identify determinants which may permit the D1 and D5 subtypes to elicit unique cellular responses.

SUMMARY OF THE INVENTION

A number of cDNA clones whose products may interact with D1 receptors in vivo were identified. One of the clones, K37, was characterized further. The protein (P24) encoded by K37 is localized in dendrites and spines of pyramidal cells in PFC. The extent of overlap between P24 expressing and D1 receptor expressing pyramidal cells appeared to be 100%. In contrast, only a limited number of D1 receptor antibody labeled neurons in caudate expressed P24. P24 lowers the threshold of D1 receptor response to dopamine (DA) by an order of magnitude. Sequence similarity suggests P24 is a diverged member of the RAMP family. The P24 protein is therefore referred to as a D1 DA RAMP, and was given the name Calcyon. The isolated protein and nucleotide molecule encoding the protein, as well as primers for the nucleotide, are described. The protein and compounds modifying DA binding to the receptor or calcium release which is mediated by Calcyon are useful in research studies, drug screening, and therapeutically.

BRIEF DESCRIPTION OF THE DRAWING

FIG. 1 is the nucleotide sequence, SEQ ID NO: 1 and amino acid sequence (SEQ ID NO: 2) of a D1-like dopamine receptor activity modifying protein. Optimal Kozak sequence for initiation by eukaryotic ribosomes is shown in bold letters. Putative transmembrane domains are shaded gray. A putative N-linked glycosylation site is marked with an asterisk. Putative protein kinase C phosphorylation sites are overlined.

FIG. 2 is an amino acid sequence alignment of Calcyon (P24) and neuronal dendritic proteins P19 (SEQ ID NO: 6) and P21 (SEQ ID NO: 7).

DETAILED DESCRIPTION OF THE INVENTION

Figure 3A:
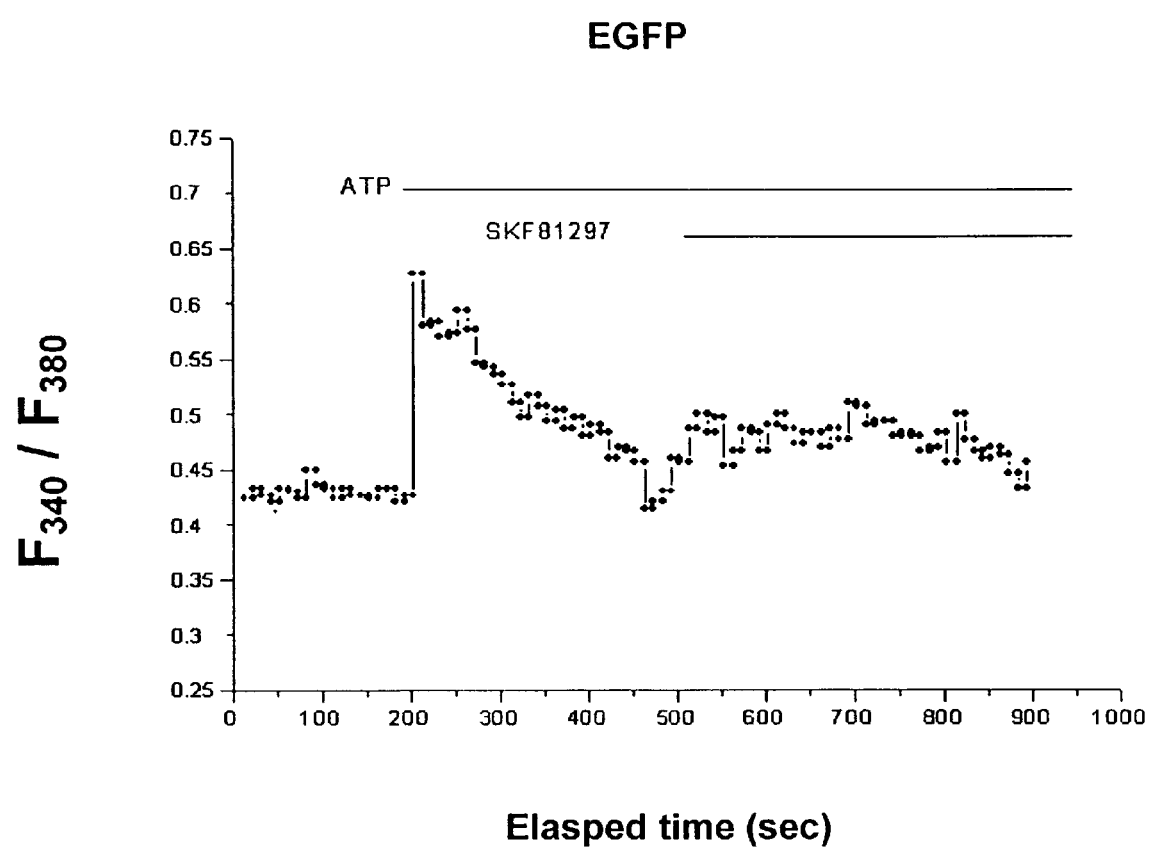
FIGS. 3a, 3b, and 3c are graphs showing that calcyon inhibits P2Y and M1 receptor stimulated $Ca^{++}_i$ release. Ligand induced $Ca^{++}$ release is shown for FURA-2-loaded D1 HEK293 cells expressing EGFP (FIG. 3a) or EGFP-Calcyon (FIGS. 3b and 3c). Substances were applied for times indicated by horizontal bar. $Ca^{++}$ signals are reported as the mean of 6–8 cells. Similar results were obtained from at least two additional transfection experiments.

I. Proteins and Processes Involved in D1 and D5 Receptor Function and Subcellular Localization Neurotransmitter receptors are typically clustered at postsynaptic membrane specializations opposed to presynaptic nerve terminals. Recent studies of the nicotinic acetylcholine (nAch), NMDA, and glycine (Gly) receptors indicate that protein:protein interactions may be important in tethering these receptors to the postsynaptic membrane. For example, a 43 kDa, zinc finger containing a protein called rapsyn appears to be absolutely essential for Ach receptor clustering at the neuromuscular junction (Froehner et al., *J. Cell Biol.* 114:1–7 (1991)). Rapsyn induces Ach receptor clustering when expressed in heterologous cells (Phillips et al., *Science* 251:568–70 (1991)); and, in rapsyn knockout mice, Ach receptors do not cluster anywhere within muscles (Gautam et al., *Nature* 377:232–6 (1995)). Likewise, clustering of Gly receptors at synaptic specializations requires accumulation of a protein expressed throughout the CNS called gephyrin (Kirsch et al., *Nature* 366:745–8 (1993)). Gephyrin copurifies with Gly receptors and also appears to associate with cytoskeletal elements (Kirsch and Betz, *J. Neurosci.* 15:4148–56 (1995). Recently, the NR2 subunit of NMDA receptors was found to interact with a postsynaptic density guanylate kinase called PSD-95. The interaction between PSD-95 and NR2 may serve to anchor NMDA receptors at the postsynaptic membrane, or assemble a multienzyme complex involved in NMDA-receptor mediated synaptic plasticity (Kornau et al., *Science* 269:1737–40 (1995)). It is not yet known if proteins analogous to gephyrin, rapsyn or PSD-95 are required for the synaptic localization of D1 or D5 receptors. On the other hand, how the D1-like receptors are directed to synapses within different membrane compartments (e.g., an apical dendritic shaft vs. spine) may involve cytosolic proteins. Such proteins may chaperone newly synthesized proteins to different areas of the plasma membrane, rather than serve as their "receptors" already in place at a given postsynaptic specialization (Casey, P. J., *Science* 268:221–5 (1995)).

Studies of the $\beta_2$-adrenergic receptor and rhodopsin indicate that GPCRs are rapidly inactivated following agonist binding, and removed from the plasma membrane to endosomes, where they are resensitized. In large part this process is mediated by two families of proteins that interact with the C-terminal tail of GPCRs. One family includes the GPCR kinases that have been found to phosphorylate rhodopsin and the $\beta_2$-adrenergic receptor at C-terminal serine and threonine residues.

The other class of proteins involved in receptor desensitization is called the arrestins. Arrestins bind GPCR kinase-phosphorylated receptors and play a key role in their removal from the plasma membrane. It has been proposed that arrestins may recruit other proteins involved in relocating receptors to endosomes, or may activate this movement themselves (Ferguson et al., *Science* 271:363–6 (1996)). Two arrestin proteins that interact with *Drosophila* rhodopsin exhibit different rates of rhodopsin inactivation suggesting multiple arrestin molecules may be required to regulated different levels of GPCR activation (Dolph et al., *Science* 260:1910–6 (1993)). Identification and characterization of GPCR kinases and arrestins that interact with the D1 and D5 DA receptors may reveal differences in D1-like receptor desensitization in vivo.

Electrophysiological studies of dissociated neostriatal medium spiny neurons suggests that D1-like receptor agonists stimulate a cascade of kinase and phosphatase activity that ultimately result in reduced N- and P-type $Ca^{++}$ currents (Surmeier et al., *Neuron* 14:385–97 (1995)). The subcellular localization of a variety of kinases and phosphatases from organisms ranging from yeast to mammals is determined by "scaffold" and "anchoring" proteins that appear to physically bring together components of coordinated, complex, signaling events. "Scaffold" proteins appear to simultaneously associate with several components of a signaling pathway (Faux and Scott, *Cell* 85:9–12 (1996)). For example, pheromones which initiate mating in yeast bind to a GPCR which results in activation of a cascade of five different kinases. The yeast protein Ste5p represents the model scaffold protein as it associates with each of these kinases. Anchoring proteins are tethered to submembranous or cytoskeletal structures, and localize a group of signal transduction enzymes to their site of action (Mochly-Rosen, *Science* 260:1910–6 (1995)). In neurons, type II cAMP dependent protein kinase (PKA) is localized to postsynaptic densities by its interaction with A-Kinase Anchoring Protein, AKAP79. Besides PKA, AKAP79 binds Ca++ calmodulin-dependent protein phosphatase 2B, calcineurin, and $\alpha$ and $\beta$ isoforms of protein kinase C (Coghlan et al., *Science* 267:108–11 (1995); Klauck et al., *Science* 271:1589–92 (1996)). Both scaffold and anchoring proteins compartmentalize functionally related enzymes, and are therefore poised to tightly regulate signaling pathways through protein-protein interactions. It is possible the kinases and phosphatases involved in D1-like receptor modulation of $Ca^{++}$ channels, and D1-like receptor may be associated with a common scaffold or anchoring protein.

II. Identifying Molecules That Interact with D1-Like Receptors

Like many cellular processes including gene transcription and synaptic vesicle targeting, there is an emerging picture that the cascade of intracellular events set off by neurotransmitter receptor activation requires large assemblies of proteins constructed of specific protein-protein interactions (Formosa et al., *In: Methods in Enzymology: Academic Press, Inc.* pp 24–45 (1991); Rothman, J. E., *Nature* 63:55–63 (1994)). By analogy with other neurotransmitter receptors, it is hypothesized that the proteins with which the D1-like receptors interact in vivo specify some aspect of D1 or D5 subtype-specific signaling or subcellular localization. Immunohistochemical analyses of the D1 and D5 receptors in the primate brain indicated that the two mammalian D1-like DA receptors may be serving subtype-specific functions due to their unique cellular and subcellular distributions (Bergson et al., *J. Neurosci.* 15:7821–36 (1995)). Molecular and cellular processes that differentially regulate D1 and D5 receptor subtype function and subcellular localization in vivo have since been identified. This research has progressed steadily as the result of developing the following tools: (1) yeast two-hybrid system for detection and analysis of D1 and D5 receptor protein:protein interactions; (2) subtype-specific monoclonal antibodies for immunochemical detection of D5 receptor: protein interactions; and (3) inducible DA receptor expression in stably transfected mammalian cells for subcellular localization analysis, ligand binding, and adenylyl cyclase assays studies. These studies provide the means to determine the requirements for multiple D1-like and D2-like subtypes.

Calcyon

Calcyon, having the amino acid (SEQ ID No. 2) shown in FIG. 1, is an example of a protein that may interact with the D1 and D5 receptors, isolated using this system.

Calcyon interacts with D1 DA receptors and enables the typically $G_s$-coupled D1 receptor to stimulate robust $Ca^{++}{}_i$ release. The results indicate that in the presence of Calcyon, D1 receptors can simultaneously activate both $Ca^{++}$ and cAMP-dependent signaling pathways. The mechanism underlying Calcyon enabled D1 receptor stimulated $Ca^{++}{}_i$ release appears to be independent of cAMP, as Calcyon expression does not alter D1 receptor-stimulated cAMP accumulation. The small rise in $Ca^{++}{}_i$ observed following D1 receptor stimulation in the absence of Calcyon may result from cAMP-dependent protein kinase (PKA) enhancement of $IP_3$ receptor-induced $Ca^{++}$ mobilization (Wojcikiewicz, R. J. H., et al., *J. Biol. Chem* 273:5670–7 (1998)). Such an indirect mechanism is likely to be temporally out of synchrony with the immediate burst of $Ca^{++}$ mobilized by D1 receptors in the presence of Calcyon. However, the mechanism likely involves binding of $IP_3$ to $IP_3$ receptors located on vesicular $Ca^{++}$ stores. The most direct means of generating $IP_3$ involves phospholipase C (PLC)-catalyzed hydrolysis of phosphatidylinositol 4,5-bisphosphate ($PIP_2$) to $IP_3$ and diacylglycerol (DAG). Stimulation of PLC is a response known to be mediated by the $G_{q/11}$ class of G proteins (Hamm, H. E., *J. Biol. Chem* 273:669–72 (1998)). Thus, it is believed that Calcyon interaction facilitates D1 receptor coupling to members of the $G_{q/11}$ family of G proteins, without disabling receptor coupling to $G_S$. Site-specific mutagenesis of the $G_q$-coupled rat M3 muscarinic receptor revealed that four residues (Arg252-Ile253-Tyr254-Lys255) (SEQ ID NO: 8) near the N-terminus of the third intracellular loop (i3) are critical for efficient $G_{q/11}$ activation and stimulation of $PIP_2$ hydrolysis (Bluml, K., et al., *J. Biol. Chem* 269, 402–5 (1994)). This sequence is also present in the analogous region of the $G_q$-coupled M1 and M5 receptors (Blin, N., et al., *J. Biol. Chem* 270:

17741–8 (1995)). The D1 receptor contains an almost identical sequence (Arg216-Ile217-Tyr218-Arg219) (SEQ ID NO: 9) located at the N-terminus of i3.

Calcyon-enabled, D1 receptor-stimulated $Ca^{++}$ release occurs after prior activation of a $G_q$ coupled GPCR. $G_q$-coupled GPCR stimulation leads to PKC activation via DAG and $Ca^{++}$ generation (Oancea, E., et al., *Cell* 95:307–18 (1998)). Although Calcyon is phosphorylated in unstimulated cells, the level of Calcyon phosphorylation increases following treatment with the PKC activator, PMA. Therefore, $G_q$ coupled GPCR activation may be necessary to stimulate PKC-dependent phosphorylation of Calcyon. PKC inhibition prevents Calcyon-enabled, D1 receptor-stimulated $Ca^{++}$ mobilization, consistent with this idea. BLAST search of the SwissProt database using the predicted intracellular domain of Calcyon revealed significant similarity between the alanine-rich region of Calcyon and the myristolated alanine-rich C kinase (PKC) substrate (MARCKS) protein. MARCKS has been shown to inhibit PLC-catalyzed hydrolysis of $PIP_2$ by sequestering $PIP_2$ (Glaser, M., et al., *J. Biol. Chem* 271:26187–93 (1996)). Because Calcyon expression decreases P2Y and M1 receptor-stimulated $Ca^{++}_i$ release, the results are consistent with the possibility that Calcyon may also sequester $PIP_2$. PKC dependent phosphorylation of MARCKS releases sequestered $PIP_2$. Reasoning by analogy, if $G_q$-coupled receptor stimulation leads to additional phosphorylation of Calcyon, the liberated pools of $PIP_2$ may contribute to the large increase in $Ca^{++}$ mobilized by D1 receptor stimulation.

Calcyon is a single transmembrane protein that exhibits extensive sequence identity with the neuronal dendritic proteins, P19 and P21. Recently, another family of single transmembrane proteins called receptor activity modifying proteins (RAMP) has been reported to regulate calcitonin-receptor-like receptor (CRLR) function (McLatchie, L. M., et al., *Nature* 393:333–9 (1998)). Peptide hormone GPCRs, like CRLR, interact with ligands through their N-terminal extracellular segments (Ji, T. H., et al., J. Biolog. Chem 273, 17299–302 (1998)). Presumably, association with the extensive extracellular domains of the RAMP family alters CRLR affinity for the calcitonin-related peptides, CGRP and adrenomedullin. On the other hand, GPCR cytoplasmic domains are crucial for specifying intracellular signaling pathways (Hamm, H. E., *J. Biol. Chem* 273, 669–72 (1998)). The data suggests that, via cytoplasmic domain interactions, Calcyon expands the repertoire of signaling possibilities for the D1 DA receptor. As such, RAMPs and Calcyon both appear to modify GPCR function, but through different mechanisms. The RAMP and P19/21/24 family of proteins display extensive sequence similarity within their predicted transmembrane segments suggesting that Calcyon is a diverged member of the RAMP family. Since D1 DA RAMP (Calcyon) is more similar to P19 and P21 proteins than to RAMP1, 2 and 3, it is proposed that the family of G-protein coupled RAMPs now includes at least two subfamilies.

The mechanism by which Calcyon alters D1 receptor and $G_q$-coupled receptor function in HEK293 cells provides a molecular framework for testing how receptors for DA, as well as for other neurotransmitters, modulate the actions of other neurotransmitters and hormones. As Calcyon is a member of a larger protein family, it seems possible that P19 and P21 may also act as 'molecular bridges' between GPCR signaling pathways. It is also possible that other neurotransmitters that regulate PKC may 'prime' the D1 receptor-stimulated $Ca^{++}$ release enabled by Calcyon. A key candidate is glutamate, as spines of pyramidal cells are the site of excitatory amino acid input. Stimulation of NMDA receptors leads to influx in $Ca^{++}$ and can result in activation of $Ca^{++}$-dependent isoforms of PKC (Oancea, E., et al., *Cell* 95:307–18 (1998)) which is an important 'priming' step in Calcyon activation. Numerous electrophysiological, as well as molecular models of synaptic plasticity indicate that D1 receptors influence NMDA receptor-mediated glutamate transmission (Cepeda, C., et al., *Synapse* 11:330–41 (1992); Cameron, D. J., et al., *Nature* 366:344–7 (1993); Huang, Y. Y., et al., *Proc. Natl. Acad. Sci. USA* 92:2446–50 (1995); Williams, G. V., et al., *Nature* 376:572–5 (1995); Konradi, C., et al., *J. Neurosci.* 16:4231–9 (1996)). As Calcyon localizes to spines of pyramidal neurons in primate prefrontal cortex, it is poised to powerfully modulate excitatory transmission. D1 (Bergson, C., et al., *J. Neurosci.* 15:7821–36 (1995)) and M1 receptors (Mrzljak, L., et al. *Proc. Natl. Acad. Sci. USA* 90:5194–8 (1993)) also localize to spines of pyramidal neurons, raising the possibility that the mechanism of muscarinic/dopaminergic 'receptor interaction' defined here may be relevant in vivo (Wang, J. Q., et al., *J. Pharmacol. Exp. Ther.* 281:972–82 (1997)). In particular, the role of Calcyon in potentiating $Ca^{++}$ signaling pathways may provide insight into the D1 receptor-dependent cognitive functions of prefrontal cortex that are compromised in schizophrenia (Williams, G. V., et al., *Nature* 376:572–5 (1995)).

Molecules that Alter Binding to Calcyon

The cDNA encoding Calcyon can be expressed in a variety of mammalian cell lines, including the fibroblast cell line described above, or in other commercially available-cell lines such as Cos cells, and used to screen for compounds which bind specifically to the Calcyon. This is determined by comparing binding affinities for the various $D_1$, $D_2$, and $D_3$ receptors with that of Calcyon, then testing in vivo those compounds which specifically bind the receptor. It can also be expressed in bacterial cells, notably *E. coli,* as well as other eukaryotic expression systems such as Baculovirus infection of insect cells.

Compounds which bind either the human or the rat Calcyon can be screened using physiological models. The typical models for physiological testing of these compounds are rats, mice and dogs. Measurements can be made in intact animals, in tissue explants or in isolated cells.

The gene and/or cDNA can also be used to generate probes for screening in a manner similar to those methods described above for receptors other than the known $D_1$, $D_2$, $D_3$, and $D_4$ dopamine receptors. Probes are created from sequences generally fourteen to seventeen nucleotides in length, and can be labelled using available technology and reagents, including radiolabels, dyes, tomography positron emission labels, magnetic resonance imaging labels, enzymes, and fluorescent labels. Probes can be used directly or indirectly via standard methodologies including polymerase chain reaction (PCR) and methodologies to generate larger fragments of the Calcyon. Starting with either RNA (via RT PCR) or DNA, the Calcyon cDNA, and parts therein, can also be used to generate RNA transcripts if cloned into appropriate expression vectors (cRNAs).

As used herein, a primer or probe said to hybridize specifically to a particular nucleic acid fragment, sequence, or segment, or to a class of nucleic acid fragments, sequences, or segments, refers to a primer or probe that hybridizes to the particular nucleic acids and does not hybridize significantly to other nucleic acids present in the same sample under the hybridization conditions used. As used herein, significant hybridization refers to hybridization that is detectable with the detection technique being used to detect specific hybridization. It is understood that some probes and primers will hybridize specifically to particular nucleic acids under some hybridization conditions but will not hybridize specifically to those nucleic acids under different conditions. That is, the probe or primer may hybridize both to the particular nucleic acids and to other nucleic acids. Thus, a probe or primer that hybridizes specifically to particular nucleic acids under at least one set of conditions is, as used herein, a probe or primer said to hybridize specifically to the particular nucleic acids. A variety of hybridization conditions can be used to hybridize probes or primers to nucleic acids.

Calcyon DNA fragments, oligonucleotide probes or cRNAs, could all be used in commercial kits or sold separately to measure Calcyon transcript levels using standard techniques including PCR, in situ hybridization, and RNAse or SI protection assays.

Amino acid sequence can be deduced from fragments of Calcyon, or the entire Calcyon coding sequence, generated by a variety of standard techniques for synthesis of synthetic peptides, Calcyon fusion proteins and/or purification of Calcyon proteins (or parts thereof) from in vitro translated proteins derived from synthetic Calcyon RNA or protein purification per se. Calcyon proteins, peptides, fusion proteins or fragments thereof could subsequently be used for antibody production using available technology including injection into a wide variety of species including mice, rats, rabbits, guinea pigs, goats, etc. for the production of polyclonal antisera as well as injection into mice and subsequent utilization of fusion techniques for the production of monoclonal antibodies.

Oligonucleotides or larger sequences derived from Calcyon mRNA or complementary sequences or antibodies directed against Calcyon could be labelled or derivatized to be used as imaging agents for positron emission tomography (PET) or magnetic resonance imaging (MRI) of the location of Calcyon in vivo and in vitro.

Diagnostic and Therapeutic Applications

As demonstrated in the examples, Calcyon plays a role in DA binding and calcium release. Compounds which alter Calcyon activity or calcyon mediated activity, can therefore be used in research or in therapeutic applications similar to those in which other RAMP proteins are utilized. These compounds can be identified as described above and in more detail below.

EXAMPLES

The present invention will be further understood by reference to the following non-limiting examples.

Example 1

Characterization of cDNA Clones Isolated in a Two-Hybrid Screen for Proteins that Interact with the hD1 Dopamine Receptor Yeast two-hybrid systems are useful for detection and analysis of D1 and D5 receptor protein:protein interactions. The two-hybrid system, initially described in yeast *Saccharomyces cerevisiae,* is a powerful molecular genetic technique for identifying new regulatory molecules, specific to the protein of interest (Fields and Song, *Nature* 340:245–6 (1989)). Typically, these regulatory proteins could not have been identified using previous biochemical techniques like immunoprecipitation or cofractionation. This method has successfully led to the identification of proteins associated with NMDA receptor NR2 subunits (Komau et al., *Science* 269:1737–40 (1995), Huntington's protein (Li et al., *Nature* 378:398–402 (1995)), Fragile X Mental Retardation Syndrome gene product (Zhang et al., *EMBO J.* 14:5358–66 (1995)), in addition to the D2 long DA receptor (Pepperl et al., *Soc. Neurosci. Ann. Mtg., San Diego* Abstract 253:11 (1995)).

Two-hybrid screens are currently the most sensitive method for identifying novel protein:protein interactions. Exploiting this method represents a unique opportunity to identify proteins that interact with the D1 and D5 receptors. If proteins are involved in their transport, or localization in spines and dendrites, then it seems reasonable to expect that proteins which specify the differential subcellular localization of D1 and D5 receptors may be identified. In addition, two-hybrid screens may also identify novel heterotrimeric G-protein isoforms that may specify their differential coupling to the cAMP signal transduction pathway, or identify proteins that regulate that interaction, e.g. a novel receptor kinase or phosphatase. There are also a number of biochemical approaches for identifying proteins that interact with the D1-like receptors, including coimmunoprecipitation and affinity chromatography. A two-hybrid system for isolating and understanding the molecular and cellular determinants that contribute to the different function and subcellular localization of the D1-like subtypes in vivo involves the following steps:

1. isolating positive cDNA clones isolated in a yeast two-hybrid screen of a human brain GAL4 activation domain library with the C-terminus of the D1 receptor and/or the C-terminus of the D5 receptor,
2. characterizing the isolated clones by determining the DNA sequence of positive clones,
3. obtaining full-length cDNA clones,
4. determining the tissue and brain regional expression pattern of positive clones,
5. co-localizing D1 and D5 receptors and positive clones in brain sections and transfected cells, and
6. characterizing how interacting protein influences coupling/binding/localization of D1 and D5 receptors.

Methods other than a two-hybrid system can also be used to identify molecules that interact with the D1-like receptors. For example, immunoprecipitation or cofractionation have been used to isolate numerous biological macromolecules. Affinity chromatography can also be used to isolate biological macromolecules. Standard genetic screens can also be used in certain organisms, such as yeast, to isolate molecules involved in metabolic pathways.

A general example of how an immunoprecipitation method could be used is as follows. Monoclonal antibodies to D5 receptors can be used to isolate interacting proteins by coimmunoprecipitation. Molecules that coimmunoprecipitate can be purified and then microsequenced by performing tryptic digests. This information can be used to develop oligonucleotides which can be used to screen cDNA libraries to isolate positive clones. These clones can then be characterized.

A general example of an affinity chromatography method is as follows. D5 receptor fusion proteins immobilized to an agarose matrix can be used to isolate interacting proteins. The microsequence of the isolated proteins can then be determined using tryptic analysis, and the protein sequence information can be used to obtain oligonucleotide probes. These probes can be used to obtain cDNA clones. The cDNA clones can be isolated and sequenced. The interactions can also be functionally characterized.

I. D1 Receptor:GAL4 DNA Binding Domain Fusion Protein

Sequence encoding C-terminal 81 amino acids of the hD1 receptor (residues 365–446) was subcloned into the yeast GAL4 DNA binding domain plasmid pGBT9, creating pGBTD1 (Fields and Song, 1995). A 252 base pair EcoRI-Sal I fragment encoding the C-terminal 81 amino acids of the human D1 receptor was inserted into the multiple cloning site of pGBT9 at the 3' end of the open reading frame for the GAL4 DNA binding domain. Transcription of the fusion gene is activated by the constitutive ADH1 promoter, $P_{ADH1}$; and terminated at the ADH1 transcription termination signal, $T_{ADH1}$. The plasmid contains selectable marker trp1 for growth on media lacking tryptophan (-trp). Yeast strain Y190 cells transformed with pGBTD1 were reacted with rabbit anti-D1 receptor antibodies and Cy3-conjugated goat anti-rabbit secondary antibody, then stained with DAPI. Cy3 and DAPI fluorescence showed coincident labeling of yeast nuclei by both D1 antibodies and DAPI. Cy3 fluorescence was not detectable in Y190 cells transformed with pGBT9 vector DNA, following similar incubation with anti-D1 and Cy3-conjugated antibodies.

The D1/GAL4 BD fusion was further tested for its ability to activate transcription of a lacZ reporter gene located on the Y190 chromosome using the X-Gal colony filter assay. pGBTD1 did not activate β-galactosidase transcription alone, or if co-expressed with GAL4 Activation Domain (AD) protein encoded on the vector pGAD424. The nuclear localization, and lack of independent lacZ expression of the D1/GAL4 BD fusion protein confirmed that it would be possible to detect interacting GAL4 AD fusion proteins.

Cotransformants of pGBTD1 and pGAD424 were streaked on SC-Trp, -Leu media. pGAD424 carries the leu2 gene for selection. As a positive control, Y190 transformed with yeast interacting proteins snf1 and snf4 were also streaked on the plate (snf1+snf4). A nitrocellulose filter was placed on the plate to transfer the colonies to the filter. Cells were permeabilized by freezing in liquid nitrogen, and then soaked in buffer containing X-Gal. Colonies containing the D1/GAL4 BD fusion protein remained cream colored, showing that the D1/GAL4 BD protein does not independently stimulate β-galactosidase gene transcription. In contrast, the positive control colonies, snf1+snf4, turned deep blue. The results show the lack of independent lacZ expression of the D1/GAL4 BD fusion protein.

This segment of the D1 receptor exhibits <20% amino acid sequence similarity with the analogous region of the D5 receptor. The yeast strain Y190 was transformed with pGBTD1 using the lithium acetate/glycerol procedure (Chen et al., Current Genetics 21:83–4 (1992)). pGBT9 contains the trp1 marker which allows selection for plasmid uptake. Transformed cells were selected for on SC-Trp medium. The D1:GAL4 fusion protein was localized in nuclei of Trp+ transformed Y190. Therefore, the D1/GAL4 BD fusion protein is appropriately localized for contact with candidate interacting proteins fused to GAL4 Activation Domain (AD) in a two-hybrid screen.

II. Screen of Human Brain cDNA:GAL4 Activation Domain Library with pGBTD1.

A human brain cDNA library in the GAL4 activation domain vector, pACT2, was purchased from Clontech (Palo Alto, Calif.). This library consists of $5.0 \times 10^6$ independent clones with inserts ranging in size from 0.5–4.5 kb. 500 μg pACT2 library plasmid DNA purified from $8 \times 10^6$ recombinant cDNA clones was transformed into the pGBTD1 transformed Y190 described above (Allen et. TIBS, December, 1995, pp. 511–516). Transformants containing pGBT9 and recombinant pACT2 were plated on 50 150 mm plates containing SC-Trp, -Leu media, grown for three days at 30°, and then assayed for β-galactosidase activity. Blue colonies were taken either directly from the filter or from the original plate, streaked for single colonies and re-tested for β-galactosidase activity in the X-Gal filter assay. 25 Leu+,Trp+ transformants exhibited detectable levels of lacZ gene expression after three rounds of single colony cloning. Nitrocellulose lifts, β-galactosidase activity assays, and growth on leu-trp-his-plates in the presence of 30 mM and 100 mM 3-amino-1,2,4-triazole were done as described by Durfee et al., Genes Dev. 7:555–69 (1993). The nucleotide sequence of both strands of pACTP24 insert DNA was determined using an ABI Automated DNA Sequencer. Protein sequences were aligned using CLUSTALW program on the EBI, UK server, and BOXSHADE 3.21 program on the ISREC, Switzerland server.

III. Genetic Characterization of Interacting Activation Domain cDNA Clones

To test whether lacZ expression depended on coexpression of the GAL4 binding domain, the pGBTD1 plasmid was eliminated from these clones. Loss of pGBTD1 was accomplished by streaking single clones on rich YEPD medium, and replica plating on SC-Trp, SC-Leu, and SC-Trp-Leu media. Colonies that grew on SC-Leu, but not on SC-Trp or SC-Trp, -Leu had lost the TRP marker (pGBT9), but retained the library pACT2 plasmid. These Leu+ colonies were picked, streaked on SC-Leu medium, and assayed for β-galactosidase activity. Of the 25 Leu+ clones picked, only one exhibited GAL4 binding domain independent lacZ gene expression by the X-GAL filter assay. This clone was eliminated from further analysis.

Transcription of the his3 gene in yeast strain Y190 is regulated by the GAL4 upstream activator sequence. Therefore, D1:AD clone interactions can also be "selected" for by plating on SC-Trp, -Leu, -His media containing 3-aminotriazole (3-AT), a competitive inhibitor of histidine. 100 mM is considered a stringent concentration of 3-AT, and 30 mM less stringent. Comparison of growth on SC-Trp, -Leu, -His+100 mM 3-AT versus SC-Trp, -Leu, -His+30 mM 3-AT provides a preliminary means of evaluating the strength of interaction between activation domain clones and D1 sequences. Eight of the 24 Leu+, Trp+ transformants were streaked on +30 and +100 mM 3-AT media. Six of the eight grew equally well on SC-Trp, -Leu, -His+30 mM and +100 mM 3-AT plates indicating very strong interaction between these clones and the D1 C-terminus. While the other two thrived on the +100 mM 3-AT plates, they grew better on +30 mM 3-AT plates indicating that the interaction may not be as strong.

The specificity of interaction between the recombinant AD clones and the D1 C-terminus was also tested by asking whether the AD clones interact with unrelated GAL4BD fusions. AD clones were tested with p53, casein dependent kinase 2 (cdk2), and snf 1 GAL4 binding domain fusions. Leu+Y190 colonies containing recombinant AD clones corresponding to eight of the clones that grew on 3-AT were mated with Trp+Y 187 strains transformed with either p53:, cdk2:, or snf1:GAL4 BD plasmids. None grew on SC-Trp, -Leu, -His +100 mM or 30 mM 3-AT media. Lack of growth indicates that these eight library clones do not interact with either p53, cdk2, or snf1, adding further confidence in the specificity of interactions with D1 C-terminal residues. The remaining sixteen AD clones were being tested for growth on -His +30 and +100 mM 3-AT media, and interaction with unrelated GAL4 BD fusions.

IV. Molecular Characterization of Interacting Activation Domain cDNA Clones

Recombinant pACT2 activation domain plasmid DNA was purified from the above eight Leu+Y190 and transformed into *E. coli* strain DH5 by electroporation. The size of the cDNA insert was determined by PCR using primers complementary to 5' and 3' vector sequences flanking the multiple cloning site. Insert sizes ranged from 500 bp to 1.8 kb.

Partial nucleotide sequence of the eight candidate positive clones was obtained using the ABI system at the Macromolecular Core Facility at Penn State College of Medicine. The sequence of the GAL4 activation domain cDNA inserts was determined using an oligonucleotide primer complementary to vector sequence located 5' of the multiple cloning site. A BLAST search of the GenBank, as well as the EST and STS databases was conducted with the DNA sequence of each insert. BLAST analysis of some clones revealed sequence similarity with known proteins, or with cDNA clones isolated in the human brain expressed sequence tag (EST) project. The sequences of other activation domain clones are novel. Although the homologies detected are based on DNA sequences obtained from sequencing one strand, several cDNAs seem to encode proteins with potentially relevant functions. For example, clone K37 exhibits extensive sequence identity with a family of related proteins variously called 21K, human brain neuronal protein-1, and 19K Golgi protein (Sutcliffe et al., *Cell* 33:671–82 (1983); Saberan-Djoneidi et al., *J. Biolog. Chem.* 270:1888–93 (1995). The 19K Golgi protein is expressed in the Golgi apparatus of neural cells (Saberan-Djoneidi et al., *J. Biolog. Chem.* 270:1888–93 (1995)).

Immunohistochemical studies with peptide antibodies to brain neuronal protein-1 revealed labeling of many large projection neurons including pyramidal neurons. Antibody reactivity was concentrated in cytoplasm with a polarity that suggested that BNP-1 may be involved in synthesis of proteins destined for dendrites (Sutcliffe et al., *Cell* 33:671–82 (1983)). The sequence of 21K has not been published, but is entered in the GenBank database (accession #M98530). The 21K gene maps next to the Huntington's Disease marker D4S10, and shows homology with protein phosphatase inhibitors.

Clone #24–29 exhibits extensive sequence identity to an EST clone that is similar to a zinc finger protein called rhombotin-1, and to rhombotin-1 itself. Rhombotin-1 is expressed mainly in the central nervous system and thymus (Boehm et al.,*Oncogene* 6:695–703 (1991)). In addition, clone #24–29 exhibits sequence similarity with the cysteine rich zinc finger region, of two human lim domain proteins hLH-1 and hLH-2. The zinc finger region in these proteins, called a LIM domain, is thought to be involved in protein: protein interaction. A variety of LIM domain proteins have been isolated. Functions associated with LIM-domain proteins include development, cytoskeletal structure, signaling and trafficking, and growth control (Gill, G. N., *Structure* 3:1285–9 (1995)). It may also be noteworthy that rapsyn is also a zinc finger protein (Froehner, 1991).

Results of BLAST analysis suggest that clones J48 and F41 may be overlapping and encode novel proteins as both share only limited sequence identity with two EST clones D79577 and AA060454. Neither clone exhibits strong identity with any known protein motifs. Similarly, clones i33b and F44a appear to be overlapping cDNA clones. One segment of both clones is virtually identical to regions within EST cDNA clones N70566 and F13805. EST clones N70566 and F13805 also overlap. Clones i33b and F44a do not appear to contain sequence motifs found in any known proteins. The products of i33b and F44a are expected to be novel. On the other hand, clones D21 and #23–15 appear to be overlapping and encode a novel protein with some homology to a frog neuronal intermediate filament protein.

Example 2

Characterization of P24

I Sequence analysis

The 936 bp cDNA contained a single 651 bp long open reading frame(ORF) encoding a 217 residue protein P24 with a single transmembrane domain. The P24 protein sequence also includes sites for N-linked glycosylation, protein kinase C phosphorylation, and vesicular transport and sorting (Kyte, J., et al., *J. Mol. Biol.* 157:105–32 (1982)).

BLAST searches revealed a high degree of sequence similarity with neuronal dendritic proteins, P19 (Wang, H. Y., et al., *Mol. Pharmacol.* 48:988–94 (1995)) and P21 (Yu, P. Y., et al., *J. Clin. Invest.* 95:304–8 (1995); Lefkowitz, R. J., *J. Biol. Chem.* 273:18677–80 (1998)). P24 appears to be a more distant relative of this family as the P24 amino acid sequence exhibits approximately 37% sequence identity to these proteins, whereas the sequences of P19 and P21 are approximately 55% identical.

II. P24 Interacts with D1 Receptors

A. Pull-down Assays

For pull-down assays, a 550 bp Nco I-Bgl II fragment from pACT-Calcyon was subcloned into pET30a (Novagen, Madison, Wis.) to produce the S-Calcyon fusion protein containing residues 93–217 of the predicted Calcyon protein as well as an N-terminal tag composed of the 15 residue S peptide of ribonuclease S (Richards, F. M., et al., The Enzymes. ed.: Boyer, P. D., Academic Press, N.Y., pp. 647–806 (1971)). The S-β-galactosidase fusion protein was composed of bacterial β-galactosidase protein tagged at its N-terminus with the S peptide. Fusion proteins were induced in BL21(DE3) *E. coli* with IPTG, and coupled to S-agarose resin (Novagen, Madison, Wis.) by incubating soluble fractions of bacterial lysates with resin for 1 h at RT. Following incubation, unbound proteins were eliminated by washing the resin three times in 50 volumes of 25 mM HEPES (pH 7.4), 50 mM NaCl. Interaction assays were performed with GSTD1 purified as described (Bergson, C., et al., *J. Neurosci.* 15:7821–36 (1995)) or solubilized lysates of D1 HEK293 cells in 25 mM HEPES (pH 7.4), 50 mM NaCl, 10% glycerol, 1% bovine serum albumin containing 0.5% NP-40. Peptide1 421–435 (SVILDYDTDVSLEKI) (SEQ ID NO. 3) and Peptide2 (NEDQKIGIEIIKRALKI) (SEQ ID NO. 4) were synthesized using an Applied Biosystems 430A Peptide Synthesizer using the FastMoc procedures and reagents supplied by Perkin-Elmer, Applied Biosystems division. Peptides were resuspended in 100 mM HEPES, pH 7.4 at 1 mg/ml prior to addition to 'pull-down' reactions. S-protein bound resin and protein targets were mutated for 2 h at RT, washed twice in 10 volumes 25 mM HEPES (pH 7.4), 50 mM NaCl, then resuspended in gel loading buffer (Laemmli, U. K., *Nature* 227:680–5 (1970)).

B. In vivo Labeling and Immunoprecipitation

Approximately 40 h after transfection, pEGFP or pEGFP-Calcyon transfected D1 HEK293 cells were washed and placed in HBS (phosphate-free media) for 1.5 h prior to addition of [$^{32}$p] orthophosphate (135 µCi/ml). 2 h later, cells were treated with 100 nM PMA (Phorbol 12-Myristate 13-Acetate) in HBS for 0.5 h at 37°. Cells were then washed once in cold PBS and solubilized in mild lysis solution (Cytosignal, Irvine, Calif.) containing protease inhibitor cocktail (Boehringer Manheim) and phosphatase inhibitors, 50 µM NaF and 5 µM EGTA. Lysates were centrifuged for 5 min at 14,000 rpm and the supernatant was incubated at RT. for 1 h with mouse anti-GFP mab (Clontech, Palo Alto, Calif.) (diluted 1:100), followed by 0.02 volume of protein A/G agarose slurry for 30 min. The resin was washed twice with mild lysis solution, and adsorbed proteins eluted in SDS PAGE loading buffer (Laemmli, U. K., Nature 227: 680–5 (1970)). Samples were analyzed by SDS-PAGE, using a 15% gel (Bio-Rad). The gel was dried and visualized using a Phosphorimager SF (Molecular Dynamics). Values pixel intensity were obtained by "boxing" the bands and subtracting the lane background using Image Quant v. 3.3 software (Molecular Dynamics).

C. Functional Characterization

A series of experiments were then undertaken to functionally characterize the interaction between P24 and D1 receptor proteins. D1-HEK293 cells, a HEK293 cell line that expresses hD1 receptors, and pEGFP-P24 expression plasmid were used for these studies. pEGFP-P24 encodes P24 protein tagged at its N-terminus by enhanced green fluorescent protein (EGFP). The N-terminal EGFP tag allowed testing to determine whether P24 directly associates with D1 DA receptors when coexpressed in mammalian cells in a "pull-down" assay. D1 receptors co-immunoprecipitated with EGFP-P24 fusion protein transiently expressed in transfected D1-HEK293 cells, and were "pulled down" by GFP mab. In contrast, D1 receptors did not co-immunoprecipitate with EGFP, although the GFP mab immunoprecipitated EGFP from pEGFP-C3 transfected D1-HEK293 cells.

A family of single transmembrane proteins called receptor activity modifying proteins (RAMP) has been found to increase the sensitivity of calcitonin-like peptide GPCR family to the various endogenous peptide ligands. These results imply localization of the P24 to D1-HEK293 cell plasma membranes specifically requires interaction with D1 receptors since the HEK293 cell line used here endogenously express several other types of GPCRs including $\beta_2$-adrenergic, muscarinic, purinergic and prostaglandin receptors (Wang et al., J. Biol. Chem., 272:26040–26048 (1995)). Regional comparison of relative rates of DA release and re-uptake favor a synaptic mode of DA transmission in caudate, whereas nonsynaptic DA transmission is thought to be the norm in PFC. Antibodies to a 20 residue segment of P24 were developed to characterize its interaction with D1 receptors. Affinity-purified P24 antibodies bound to a strong band of approximately 34K present in microsomal protein fractions purified from rhesus monkey PFC and caudate putamen, but not spleen. Incubation of antibodies with immunizing peptide conjugated to BSA, but not with BSA alone, prior to immunoblotting, prevented detection of the approximately 34K band. P24 antibodies reacted with an approximately 24K PFC microsomal protein digested with PNGaseF, suggesting the 34K band corresponded to P24 protein modified by N-linked oligosaccarhides. The size of the deglycosylated protein agrees with the predicted molecular weight of the P24 core protein. The P24 antibody reactive protein proved resistant to solubilization following treatment of microsomal fractions with chaotropic agents, including 100 mM $NaCO_2$, suggesting P24 spans a phospholipid bilayer. Taken together our data support the prediction that P24 is an N-linked glycosylated, transmembrane protein.

To pinpoint the binding site for Calcyon, shorter fragments of the 81 residue D1 receptor bait, $pGBTD1_{365-446}$, were tested for interaction with pACTCalcyon by the two-hybrid assay. Deletion of the C-terminal 11 amino acids had no apparent effect on the ability of the D1 receptor bait to interact with Calcyon as $pGBTD1_{365-435}$ and pACTCalcyon stimulated lacZ expression when cotransformed into yeast. However, deletion of 26 residues from the C-terminus of the D1 receptor prevented detectable interaction between $pGBTD1_{365-420}$ and pACTCalcyon. In contrast, the Calcyon:GAL4 AD fusion protein interacted with D1 receptor:GAL4 binding domain fusion proteins, encoded by $pGBTD1_{421-446}$ and $pGBTD1_{421-435}$, in which the N-terminal 55 residues of the D1 'bait' were deleted. These results suggest residues 421–435 of the D1 receptor comprise a minimal domain sufficient for interaction with Calcyon.

The interaction between Calcyon and D1 receptor was confirmed in 'pull-down' assays. The predicted Calcyon cytoplasmic domain was fused to the 15 residue S protein recognition sequence (Richards, F. M., et al., The Enzymes. ed.: Boyer, P. D., Academic Press, NY, pp. 647–806 (1971)), and the resulting fusion protein, designated S-Calcyon, was immobilized with S-agarose resin. An unrelated fusion protein S-β-galactosidase, served as a negative control. The ability of the S-tagged proteins to associate with a glutathione-S-transferase-D1 (GSTD1) fusion protein containing the 81 residue D1 receptor 'bait' sequence was tested by incubating GSTD1 with immobilized S-Calcyon and S-β-galactosidase. Immunoblots of proteins eluted from the S-agarose resins were probed with D1 receptor antibodies.

D1 antibodies bound to a band of approximately 36 K, the size predicted for the fusion protein, in the positive control lane containing purified GSTD1. A D1 antibody reactive band of similar size was present in lanes containing eluate from immobilized S-Calcyon suggesting the protein 'pulled-down' by S-Calcyon corresponded to the GSTD1 fusion protein. In contrast, the immunoreactive band was not present in lanes containing eluate from S-β-galactosidase-bound resin. As coomassie staining revealed equivalent levels of the S-tagged fusion proteins bound to the S-agarose resin, the ability of S-Calycon to 'pull-down' pGBTD1 presumably reflects the higher affinity of D1 receptor C-terminal sequences for associating with S-Calcyon than S-β-galactosidase. To confirm the necessity of D1 receptor sequences, pull-down assays were performed in the presence of a peptide containing D1 receptor residues 421–435 (pep421–435), or an unrelated 17 residue peptide, pep2. Pep421–435, but not pep2, prevented detection of the immunoreactive GSTD1 band suggesting pep421–435 can block interaction between GSTD1 and S-Calcyon. These results further support a role for D1 receptor residues 421–435 in mediating interactions between the D1 receptor and Calcyon. In,addition, the results of these in vitro experiments indicate the Calcyon interacts with D1 receptors through its C-terminal segment.

A human embryonic kidney (HEK) 293 cell line, designated D1 HEK293, that stably expresses hD1 receptors was used to test the ability of S-Calcyon to interact with full-length D1 DA receptors. Detergent solubilized lysates of D1 HEK293 cells were incubated with resin-immobilized S-Calcyon and S-β-galactosidase. Proteins retained by the S-tagged target polypeptides were analyzed by immunoblotting with D1 receptor antibodies as described above. Full-length D1 receptor polypeptide migrates with a molecular mass of approximately 48–50 K in D1 HEK293 cell lysates. Bands of similar size were also present in lanes containing D1 HEK293 cell proteins 'pulled-down' by S-Calcyon. In contrast, immunoblot lanes containing proteins 'pulled-down' by S-β-galactosidase were devoid of D1 antibody reactive bands. Taken together, the 'pull-down' studies provide further support for the direct physical interaction between D1 receptor and Calcyon proteins.

III. Distribution of P24

A. General Distribution

A 470 nucleotide Sal I-Bgl 11 restriction fragment of P24 was extracted (Qiagen) from agarose and random primer-labeled (Life Technologies) with [α-$^{32}$P]dCTP (Amersham) and purified by a Chroma Spin column (Clontech). The human RNA master blot (Clontech) was prehybridized in ExpressHyb solution (Clontech) containing 0.1 mg/ml sheared salmon testes DNA, and hybridized overnight at 65° C., with probe ($6 \times 10^6$ cpm/ml) in prehybridization solution containing 30 mg $C_0$t-1 DNA (Life Technologies), and 0.2×SSC. The filter was washed four times in 2×SSC, 1% SDS at 65° C., and two times in 0.1×SSC, 0.5% SDS at 55° C. prior to exposure to Biomax MS film (Kodak) with an intensifying screen at −85° C.

Hybridization of the $^{32}$P-labelled probes to a human RNA dot blot indicated that gene encoding the clone designated P24 was expressed in a number of the same brain regions and peripheral tissues as the D1 receptor. The strongest hybridization signals corresponded to P24 probe bound to polyA+ RNA purified from caudate/putamen, frontal lobe, subthalamic nucleus, substantia nigra, and kidney.

B. Distribution of P24 in Rhesus Monkey Brain

The distribution of P24 protein in rhesus monkey brain was determined. P24 antibodies produced immunostaining of neurons in numerous brain regions including the dopaminoceptive caudate nucleus and PFC. P24 antibodies labeled cell bodies and dendrites of pyramidal neurons in all layers of PFC, similar to previous descriptions of D1 DA receptor antibody labeling of the primate cortex (Huang, Y. Y., et al., Proc. Natl. Acad. Sci. USA 92, 2446–50 (1995); Saberan-Djoneidi, D., et al., J. Biol. Chem 270 1888–93 (1995)).

Three female New Zealand White rabbits were immunized with Keyhold limpet hemocyanin (KLH) conjugated to a twenty residue peptide (NH$_2$-QLSSPDQQNFP-DLEGQRLNC-COOH) (SEQ ID NO: 5). P24-specific antibodies were affinity-purified from crude serum using BSA-conjugated peptide coupled to affigel-15 (Biorad). Perfusion and preparation of brain tissue from adult macaque monkeys (Macaca mulatta) was carried out as described by Mrzljak et al., 1996. 40 µm sections were incubated with P24 antibodies for 48 h (4° C.), and processed by the avidin-biotin method using horseradish peroxidase with an ABC Elite kit (Vector Labs). For double-labeling experiments, sections were incubated with a cocktail of rat D1 monoclonal antibody (RBI), and rabbit P24 antibodies, washed, and incubated with Cy3-conjugated or FITC-conjugated secondary antibodies (Jackson Immunoresearch). Sections were viewed with Molecular Dynamic confocal argon/krypton laser and Nikon Diaphot 200 microscope, and data collected was collected using Molecular Dynamics Image Space software, and analyzed as a Ray Model projection of thirty mm sections.

Proteins were prepared from monkey tissues. PNGaseF (Boehringer Manheim) digestion of membrane protein fractions was carried out according to the manufacturer's instructions with 1.0 unit recombinant N-glycosidase F. Crude microsomal protein fractions of transfected HEK293 cells were isolated. The pellet was resuspended in homogenizing buffer, and protein concentrations determined. For immunoblotting, proteins were solubilized in 2×SDS Page loading buffer (Laemmli, U. K. Nature 227:680–5 (1970)), and separated by SDS-PAGE and transferred to PVDF (ICN Biomedicals) sheets (Towbin, et al., Proc. Natl. Acad. Sci. USA 76:4350–4 (1979)). Immunoblots were incubated with either rabbit antibodies to P24 (1:100) or D1 receptor mab (1:100) (RBI), and processed. Bound antibodies were detected by enhanced chemiluminescence (ECL) using an ECL plus kit (Amersham) and Hyperfilm (Amersham).

Membrane and soluble proteins were prepared from monkey tissues and stored at −75° C. as described by Mrzljak, L., et al., Nature 381, 245–8 (1966). N-glycosidase F (Boehringer Manheim) digestion of 100 µg membrane protein fractions was carried out according to the manufacturer's instructions using 1.0 unit of recombinant enzyme. Peripheral membrane proteins were dislodged from prefrontal cortex membrane protein fractions by resuspending microsomal protein pellets in 100 mM Na$_2$CO$_3$ pH 11, or 10 mM HEPES, pH 7.4, 5 mM EDTA buffer containing 500 mM NaCl, 6 M urea, 200 mM Na$_2$SO$_4$, 100 mM NaBr, or 100 mM NaI followed by centrifugation, and recovery of soluble and sedimented fractions. For immunoblotting, proteins in loading buffer (Laemmli, U. K., Nature 227, 680–5 (1970)) were separated by SDS-PAGE and transferred to PVDF (ICN Biomedicals) sheets (Towbin, H., Proc. Natl. Acad. Sci. USA 76, 4350–4 (1979)). Molecular mass was determined relative to mobility of Perfect protein markers (Novagen, Madison, Wis.). Immunoblots were incubated with either rabbit antibodies to Calcyon (1:100) or D1 receptor (1:100), followed by horseradish peroxides (HRP)-conjugated anti-rabbit antibodies (1:25,000) (Jackson Immunoresearch) and processed as described (Bergson, C., et al., J. Neurosci. 15, 7821–36 (1995)). For blocking experiments, diluted Calcyon antibodies were preincubated with 50 µg BSA or BSA conjugated to the immunizing peptide for 30'. Bound antibodies were detected by enhanced chemiluminescence using an ECL plus kit (Amersham).

1. Results

Immunogold electron microscopy of PFC further revealed P24 in spines of pyramidal neurons. Brain sections were double labeled with P24 rabbit antibodies and a D1 receptor rat monoclonal antibody (Yung, K. K. L., et al., Neuroscience 65: 709–730 (1995) (mab) to test the possibility that P24 protein may be expressed in D1 receptor-containing neurons. Bound P24 and D1 antibodies were detected with Cy3-conjugated anti-rabbit IgG and a fluorescent isothiocyanate (FITC)-conjugated anti-rat IgG; or, with FITC-conjugated anti-rabbit and Cy3-conjugated anti-rat secondary antibodies. Both combinations of secondary antibodies gave similar results. Overlay of the FITC and Cy3 fluorescent staining in PFC produced a yellow cellular labeling pattern indicating expression of the D1 receptors and P24 protein in the same population of pyramidal neurons. P24 antibodies also labeled D1 receptor expressing medium spiny neurons in caudate. However, unlike the cell for cell relationship observed in PFC, expression of P24 in caudate was restricted to a limited population of D1 receptor mab labeled medium spiny neurons. P24 protein's cortical versus caudate expression pattern may reflect a region specific requirement for association of P24 with D1 receptors. The coexpression of Calcyon and D1 receptors in pyramidal neurons and medium spiny neurons suggests that physical association of the two polypeptides could occur in vivo. In addition, the differential expression of Calcyon in D1 receptor containing cell populations in caudate and cerebral cortex raises the possibility that Calcyon may contribute cell-specificity to D1 receptor functions.

The distribution of D1 receptors and Calcyon protein in rhesus monkey brain were compared. Calcyon antibodies produced immunostaining of neurons in numerous brain regions including the dopaminoceptive prefrontal cortex and caudate nucleus. Calcyon antibodies labeled cell bodies and dendrites of pyramidal neurons in all layers of prefrontal cortex, in a manner similar to previous descriptions of D1 receptor antibody labeling of the primate prefrontal cortex. In pyramidal neurons, Calcyon antibody labeling of cell bodies is predominantly associated with the membranes and vesicles of the Golgi apparatus and much more sparsely with the endoplasmic reticulum. Such localization is suggestive of rapid posttranslational assembly of Calcyon and transport from the cell body. Immunogold electron microscopy of prefrontal cortex further revealed Calcyon protein in small and medium-sized dendrites and dendritic spines receiving asymmetric (excitatory) inputs. Similar to D1 receptors (Bergson, C., et al., *J. Neurosci.* 15:7821–35 (1995)), Calcyon protein was localized at the periphery of postsynaptic densities in dendritic spines, a subcellular location appropriate for association of the two polypeptides.

Example 3

Mammalian Cell Expression Studies and cAMP Assay

I. Calcium Imaging and cAMP Assays

For $Ca^{++}$ imaging, cells were rinsed with HBS (150 mM NaCl, 10 mM NaHEPES, 10 mM glucose, 2.5 mM KCI, 4 mM $CaCl_2$ and 2 mM $MgCl_2$, pH 7.4) and then loaded with 5 μM Fura-2 AM (Molecular Probes) in HBS at RT. After 20 min, cells were washed three times with HBS. Assays were performed at RT in 1.5 ml of HBS. Drugs were prepared in HBS and manually applied. For EGTA experiments, $Ca^{++}$-free HBS was prepared containing 0.25 mM EGTA. Samples were viewed with a Zeiss Axiovert 135 microscope (63×objective). Images were collected with a CCD camera connected to a Silicon Graphics workstation, and analyzed with Inovision-Ratiotool 4.3.5. Transfected cells were identified by illumination at 490 nm, and selected as areas for analysis. Cells were sequentially illuminated for less than 100 ms, first at 340 nm, and then at 380 nm (Grynkiewicz, G., et al., *J. Biol. Chem* 260, 3440–50 (1985)). Fluorescence emission at 510 nm was monitored for each excitation wavelength via the CCD camera at 10 s intervals. Average pixel intensities within 6–8 selected areas (each area corresponded to single transfected cell) for both wavelengths at each time point were digitized and stored on the computer.

For cAMP assay, cells were washed once with HBS, and then exposed to agonists, DA-HCl (Sigma), SKF-81297-HBr (RBI), ATP (Boehringer Manheim) or isoproterenol-HCI (RBI), and bisindolylmaleimide I HCl (Calbiochem) at 37° in HBS. After timed incubation, plates were placed on ice, media aspirated and cells washed once in 1.0 ml cold PBS. After aspiration, cells were lysed by addition of 0.75 ml 0.1 N HCl. Following centrifugation to pellet proteins, cAMP levels in supernatant were determined by Direct cAMP Enzyme Immunoassay Kit (Assay Designs, Inc.) according to the supplier's protocol. Protein pellets were first resuspended in boiling 10% SDS, then SDS concentration diluted to 0.9% by addition of 10 mM Tris pH 7.4, and protein concentrations determined (Bradford, M. M., Analytical Biochemistry 72, 248–54 (1976)). cAMP assays were performed in triplicate for each ligand concentration. Results (pmol cAMP/mg protein) are reported as average of three independent transfection experiments.

HEK293 cells and D1-HEK293 cells were transfected with pEGFP-P24 DNA to study the effects of P24:DI receptor interaction on protein localization by confocal microscopy. A 0.9 kb Eco RI-Xho I cDNA fragment encoding full-length P24 was isolated from pACTP24, and inserted into pEGFP-C3 (Clontech). Microsomal protein (200 mg) isolated from stably transfected D1 or D5 receptor HEK293 cell lines was pelleted, and briefly sonicated in 50 mM Tris (pH 7.4), 200 mM NaCl, 0.5% Triton™ X-100 to solubilize receptors. An equal volume of S-P22100-217 or S-β-galactosidase protein homogenate in the same buffer was combined with the solubilized transfected HEK293 cell microsomal fractions, and incubated for 2 h at 4° C. prior to addition of 0.05 volume of S-agarose slurry (Novagen). The mixture was nutated overnight to permit complex formation. The resin was washed three times in 50 mM Tris (pH 7.4), 200 mM NaCl, 0.05% Triton™ X-100, and bound proteins were eluted in SDS Page loading buffer, and immunoblotted as described above.

II. Results

The fusion protein appeared to be excluded from nuclei of both transfected cell types. In transfected HEK293 cells, fluorescent EGFP-P24 fusion protein exhibited a uniformly cytoplasmic distribution. The EGFP-P24 derived cytoplasmic fluorescence appeared more diffuse in D1-HEK293 cells than in HEK293 cells. In addition, in D1-HEK293 cells, the fluorescent signal outlined the cell's perimeter, presumably reflecting EGFP-P24 protein localized in the plasma membrane. In contrast, pEGFP-C3 vector DNA produced a ubiquitous fluorescent signal in both cell types. The dual plasma membrane/cytoplasmic localization of EGFP-P24 in D1-HEK293 cells suggests D1 receptors play a role in trafficking P24 to the plasma membrane.

Example 4

Effects of Calcyon Expression on D1 Receptor Signaling in HEK293 Cells

It was determined whether Calcyon influenced D1 receptor coupling to the cAMP second messenger system in D1 HEK293 cells transfected with expression plasmids encoding either enhanced green fluorescent protein (EGFP), or Calcyon tagged at its N-terminus by EGFP. D1 HEK293 cells do not endogenously express Calcyon protein. DA as well as D1 specific agonist, SKF81297 produced concentration dependent saturable increases in cAMP levels in D1 HEK293 cells transfected with either pEGFP or pEGFP-Calcyon. However, DA stimulated comparable levels of cAMP in both cell types suggesting that Calcyon expression does not alter D1 receptor activation of cAMP-dependent signaling pathways.

To test the possibility that Calcyon might play a role in D1 receptor stimulation of $IP_3$ turnover and resulting mobilization of $Ca^{++}_i$ stores, as reported from studies in brain (Wang, H. Y., et al., *Mol. Pharmacol.* 48:988–94 (1995)) and kidney, D1 HEK293 cells were loaded with the $Ca^{++}$ indicator dye Fura-2 AM (Grynkiewicz, G., et al., *J. Biol. Chem* 260: 3440–50 (1985)). Changes in $Ca^{++}_i$ levels were measured using ratiofluorometric imaging following bath application of ligand. Application of DA or 10:M SKF81297 produced no detectable response in untransfected D1 HEK293 cells, or cells expressing either EGFP or EGFP-Calcyon. In vivo, DA is considered primarily to be a neuromodulator. Therefore, to test whether Calcyon plays a role in the D1 receptor's ability to modulate other stimuli, we applied agonists of endogenous GPCRs prior to stimulating D1 receptors. Stimulation of endogenous P2Y purinergic receptors (Wang, Q., et al., *J. Biol. Chem.* 272:26040–8 (1997)) with ATP produced a rise in $Ca^{++}{}_i$ in D1 HEK293 cells. SKF 81297, when applied following ATP, also triggered an immediate increase in $Ca^{++}{}_{i\,in}$ EGFP-Calcyon expression D1 HEK293 cells. The response of EGFP-Calcyon expressing cells to the D1 agonist was comparable in magnitude, but longer in duration than the response produced by ATP. Similar responses were observed in cells bathed in $Ca^{++}$-free medium containing the cation chelator EGTA, suggesting the observed rises in $Ca^{++}{}_i$ likely reflect release of $Ca^{++}$ from intracellular stores rather than influx of extracellular $Ca^{++}$. Application of the D1 receptor antagonist, SCH23390, prior to ATP, blocked the response to SKF81927 further indicating a requirement for D1 receptors. In contrast, SKF81297 produced a gradual, but small increase in $Ca^{++}$ in the untransfected or pEGFP-transfected D1 HEK293 cells. Comparison of the response produced by the D1 agonist in EGFP-Calcyon expressing cells to cells expressing EGFP indicates that one function of Calcyon is to enhance the ability of D1 receptors to mobilize $Ca^{++}{}_i$.

EGFP-Calcyon transfected D1 HEK293 cells also responded to SKF81297 when applied after stimulating endogenous M1 muscarinic receptors (Wang, Q., et al., *J. Biol. Chem*, 272:26040–8 (1997)) with 10 µM carbachol. In contrast, EGFP-Calcyon transfected D1 HEK293 cells failed to respond to SKF81297 following stimulation of endogenous $\beta_2$-adrenergic receptors (Wang, Q., et al., *J. Biol. Chem*, 272:26040–8 (1997)) with 10 µM isoproterenol, although isoproterenol increased cAMP levels. As M1 muscarinic and P2Y purinergic receptors activate $G_q$, whereas $\beta_2$-adrenergic receptors activate $G_S$, these studies collectively suggest that stimulation of a $G_q$-coupled GPCR is important in the ability of Calcyon protein to potentiate D1 receptor-stimulated $Ca^{++}{}_i$ mobilization. In addition, the combination of ATP and SKF81297, stimulated comparable levels of cAMP accumulation in EGFP and EGFP-Calcyon expressing cells. As such, the burst of $Ca^{++}{}_i$ stimulated by SKF81297 in EGFP-Calcyon expressing cells appears to occur independent of $G_S$ activation of adenylyl cyclase.

The Calcyon sequence contains two consensus protein kinase C (PKC) phosphorylation sites within its predicted cytoplasmic domain. To determine if Calcyon is indeed a substrate for PKC, pEGFP-Calcyon and pEGFP-transfected D1 HEK293 cells were metabolically labeled with $^{32}P$-orthophosphate and treated with the PKC activator, phorbol 12-myristate 13-acetate (PMA). GFP mab immunoprecipated a $^{32}P$-labeled protein from pEGFP-Calcyon transfected cells with size equal to that detected by Calcyon antibodies. A $^{32}P$-labeled protein of similar mass was not present in pEGFP transfected D1-HEK293 cells. Phosphorimager analysis revealed approximately five times more label incorporated into the protein immunoprecipitated from PMA treated cells than from untreated cells suggesting Calcyon is a PKC substrate.

To test the possibility that PKC may regulate Calcyon function, D1 HEK293 cells expressing EGFP-Calcyon were treated with the PKC inhibitor, bisindolylmaleimide 1 HCl (BisI). $Ca^{++}$ mobilization induced by SKF81297 was considerably attenuated in cells treated with the PKC inhibitor. The response to D1 agonist in BisI-treated, EGFP-Calcyon expressing cells resembled the D1 receptor response stimulated in the absence of Calcyon. Likewise, BisI reduced D1 receptor-stimulated $Ca^{++}{}_i$ release in EGFP-Calcyon expressing cells treated with carbachol. These results suggest that the ability of Calcyon to potentiate D1 receptor-stimulated $Ca^{++}{}_i$ mobilization is regulated by PKC.

PKC inhibition also altered the response of the P2Y receptor. Following application of BisI, ATP stimulated a rise in $Ca^{++}{}_i$ in D1 HEK293 cells expressing EGFP-Calcyon that lasted longer than in the absence of BisI. The protracted P2Y receptor response lasted ~300–400 sec, similar in duration to the ATP response observed in EGFP expressing cells. In contrast, $Ca^{++}{}_i$ levels were typically elevated for approximately 100 sec following ATP stimulation of EGFP-Calcyon expressing cells. These results suggest that, in addition to potentiating D1 receptor-stimulated $Ca^{++}$ release, Calcyon may also suppress the ability of P2Y receptors to mobilize $Ca^{++}{}_i$. This aspect of Calcyon function also appears to be cAMP-independent as cAMP levels stimulated in response to ATP and SKF81297 in BisI-treated cells compared to untreated cells were similar. M1 muscarinic receptors appeared especially susceptible to Calcyon suppression because, in some instances, the response to carbachol was completely blocked by EGFP-Calcyon expression.

Example 5

Isolation of hD5 Receptor Monoclonal Antibody Producing Hybridoma Cell Lines

In a complementary strategy, a panel of D1 and D5 subtype-specific monoclonal antibodies (Mab) are being developed. These should be useful in isolating interacting proteins through immunoprecipitation experiments. They should also prove useful in confirming interactions with proteins identified in the yeast two-hybrid screen.

I. Characterization of hD5 Receptor Monoclonal Antibodies

Three female BalbC mice were immunized with purified MBPD5, a fusion protein consisting of hD5 receptor cDNA encoding residues 375–477 fused to the C-terminus of *E. coli* maltose binding protein (MBP) (Bergson et al., 1995b). Splenocytes of one immunized mouse were fused with P3U1 myeloma cell lines, and plated on 96 well-plates. Hybridomas were screened for antibody reactivity with GSTD5 fusion protein by ELISA, and subsequently subcloned and expanded. Specificity of the 1G1 D5 monoclonal antibody cell line, 1G1, was determined by Western blot of Sf9 cells harboring baculovirus vector containing hD1 cDNA (Bio-Signal), (D1Sf9), and CV-1 cells stably transfected with 12CA5 epitope-tagged hD5 receptor (Bergson et al., 1995b), (D5 CV-1). Membrane protein fractions (5 µg) were loaded in wells. Proteins were resolved by SDS-PAGE in a gel containing 12.5% polyacrylamide, and electroblotted to a PVDF filter. PVDF filter was blocked and reacted with 1G1 Mab, followed by biotinylated goat anti-mouse IgG (Jackson Immunoresearch). Bound 1G1 Mab was detected with an ECL kit (Amersham). The positions of Kaleidoscope (Biorad) molecular size markers were determined.

Further characterization of one clone, called 1G1, confirmed that this Mab specifically detects hD5 protein on Western blot, and quantitatively immunoprecipitates D5 receptors. 1G1 Mab reacts with a broad band of approximately 50–80 kDa present in the D5 CV-1 lane. Immunoreactivity is similar to what is observed with a rabbit polyclonal D5 receptor antibody. Diffuse, heterogeneously sized bands with mobility greater than approximately 52 kDa represent glycosylated D5 receptors (Bergson et al., 1995b). In contrast, 1G1 exhibits no detectable reactivity with D1 receptors indicating the Mab 1G1 is specific for D5 receptors. Taken together, the specificity of the 1G1 Mab as well as its ability to immunoprecipitate D5 receptors makes it a suitable reagent to isolate proteins that interact with D5 receptors by immunoprecipitation and/or immunoaffinity chromatography.

The CV-1 cell line (D5 CV-1) stably transfected with 12CA5 epitope-tagged hD5 receptor cDNA inserted into the pTetSplice expression vector (Bergson et al., 1995b; Schokett et al., *Proc. Natl. Acad. Sci. USA* 92:6522–6 (1995) was used to test whether 1G1 Mab immunoprecipitates D5 receptors. D5 receptor expression can be induced in D5 CV-1 cells by removal of tetracycline from the cell culture medium (induced D5 CV-1). If cells are grown in the presence of tetracycline D5 receptor expression is repressed (uninduced D5 CV-1). For the immunoprecipitation, 1G1 (+1G1 i.p.) or 12CA5 (+12CA5 i.p.) Mabs were added to membrane fractions of uninduced or induced D5 CV-1 cells solubilized in 1% Triton™X-100, and incubated on ice for 1 h. Following addition of 1/10 volume of protein A-Sepharose™, reactions were incubated overnight at 4° C. The next day, protein A-Sepharose™ was pelleted and washed three times in 10 mM Tris, 150 mM NaCl, pH 8.0. Crude membrane fractions from uninduced and induced D5 CV-1, and immunoprecipitated proteins (+i.p.) were solubilized in Laemmli loading buffer at room temperature for 1 h., and loaded in wells as indicated. The proteins were not boiled in loading buffer as GPCRs aggregate when boiled. Proteins were fractionated by SDS-PAGE in a gel containing 12.5% polyacrylamide, and electroblotted to a PVDF filter. The PVDF filter was blocked and reacted with 1G1 Mab, followed by biotinylated goat anti-mouse IgG (Jackson Immunoresearch). Bound antibodies were detected with an ECL kit (Amersham). D5 receptor is not detectable in uninduced cells with the 1G1 Mab, but is in the induced cells. Similarly, 1G1 quantitatively brings down D5 receptors in induced cells, but does not immunoprecipitate detectable D5 receptor from uninduced cells. 1G1 Mab immunoprecipitates proteins with mobility equivalent to that of D5 receptors expressed in induced D5 CV-1 cells. Proteins of the same size are also immunoprecipitated from induced D5 CV-1 cells by the 12CA5 Mab via the 12CA5 epitope inserted at the N-terminus of the D5 cDNA. A band of 110 kDa is present in all lanes in which immunoprecipitated protein was loaded suggesting it may correspond to unreduced IgG heavy chain dimers. (Immunoprecipitated 1G1 and 12CA5 antibodies should also be detected by the goat anti-mouse secondary antibody used for ECL detection.) Consistent with this possibility, boiling of samples in Laemmli buffer prior to SDS PAGE reduces the mobility of this band to 55 kDa, the size of heavy chain monomers.

Example 6

Mammalian Cell Culture and Immunocytochemistry

Human embryonic kidney 293 (HEK293) cells were maintained in DMEM media (Sigma) containing 2 mM glutamine, and 10% fetal calf serum. HEK293 cell lines expressing D1 or D5 dopamine receptors were established by calcium phosphate transfection (Canfield and Levenson, *Biochem.* 32:13782–6 (1993)) of pLXSN (Clontech) plasmid containing full-length human D1 (Zhou et al., *Nature* 347:76–80 (1990)) and D5 (Grandy et al., *Proc. Natl. Acad. Sci. USA* 88:9175–9 (1991)) receptor cDNAs. Stable transfected cell lines were selected in the above media containing 700 mg/ml G418 (Life Technologies), and maintained in 250 Ig/ml G418. D1 and D5 receptor expression was confirmed by Western blotting. pEGFP-C3 and pEGFP-P24 plasmid DNAs were transiently transfected into HEK293 cell lines using Effectene (Qiagen, Santa Clarita, Calif.) according to manufacturer's instructions. D1 receptor expression was confirmed by immunoblotting with receptor antibodies (Bergson, C., et al., *J. Neurosci.* 15:7821–36 (1995)). For 'pull-down' studies, approximately $10^7$ D1 HEK293 cells were scraped from dishes, pelleted, and resuspended in 25 mM HEPES (pH 7.4), 50 mM NaCl, 10% glycerol, 1% bovine serum albumin (BSA) containing 0.5% NP-40 by brief sonication. Solubilized cell lysates were obtained after a 1 h incubation on ice by pelleting insoluble fractions at 14,000 rpm for 20 min at 4° C.

pEGFP-Calcyon was created by inserting a 0.9 kb Eco RI-Xho I fragment encoding full-length Calcyon into pEGFP-C3 (Clontech). pEGFP-C3 and pEGFP-Calcyon plasmid DNAs were transiently transfected into HEK293 and D1 HEK293 cell lines using Effectene™ (Qiagen) according to manufacturer's recommendations. $2.5 \times 10^5$ cells were seeded in 6-well plates, and transfected with 0.4 :g plasmid DNA/well for $Ca^{++}$ imaging, cAMP, and immunoprecipitation assays.

Example 7

Calcyon Sequesters $PIP_2$, which is Indicative that Calcyon Could Inhibit M1 or P2Y-Stimulated $Ca^{++}_i$ Release Functional imaging studies in D1 HEK293 revealed that Calcyon enabled the D1 receptor to stimulate $Ca^{++}_i$ release following a priming step involving stimulation of either the $G_q$-coupled M1 or P2Y receptor. In addition, it was observed that Calcyon expression decreases P2Y and M1 receptor-stimulated $Ca^{++}_i$ release in D1HEK293 cells. For example, the P2Y receptor response lasted ~300–400 sec in EGFP expressing cells (FIG. 3a), whereas $Ca^{++}_i$ levels were typically elevated for less than approximately 100 sec following ATP stimulation of EGFP-Calcyon expressing cells (FIG. 3b) indicating inhibition of P2Y receptor-stimulated $Ca^{++}_i$ release by Calcyon. The M1 muscarinic receptor appears especially susceptible to Calcyon suppression because, in some instances, carbachol-stimulated $Ca^{++}_i$ release was undetectable in EGFP-Calcyon expressing D1HEK293 cells (compare FIG. 3c). These results suggested that, in addition to potentiating D1 receptor-stimulated $Ca^{++}_i$ release, Calcyon may also suppress the ability of P2Y or M1 receptors to mobilize $Ca^{++}_i$.

Figure 3B:
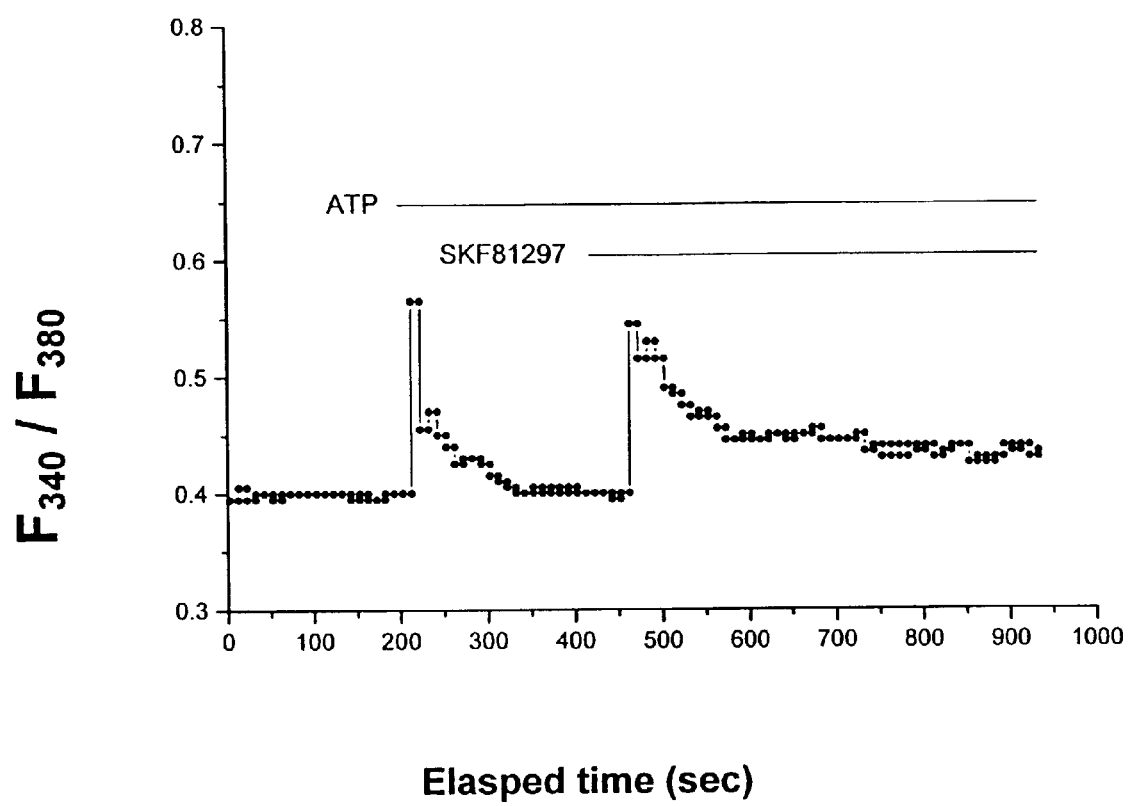
Figure 3C:
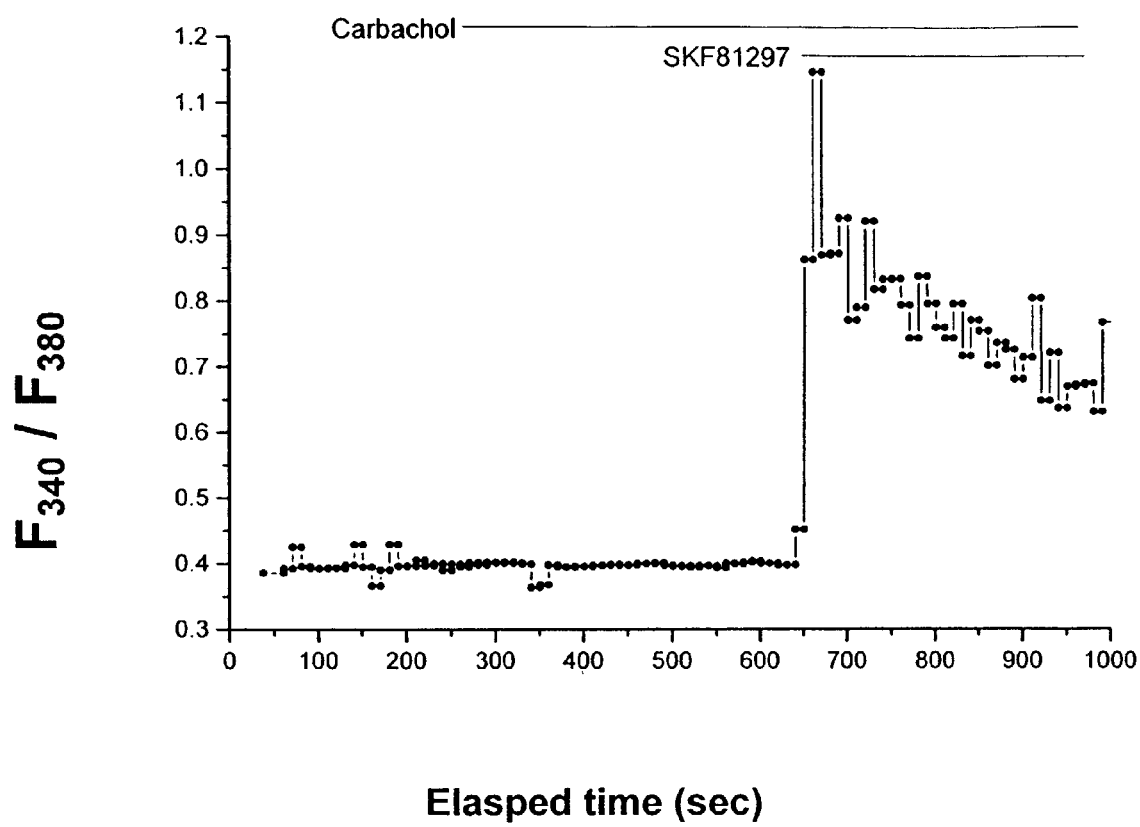

BLAST search of the SwissProt database using the predicted intracellular domain of Calcyon revealed significant similarity between the alanine-rich region of Calcyon and the myristolated alanine-rich C kinase (PKC) substrate (MARCKS) protein. MARCKS has been shown to sequester the acidic phopholipid phosphatidylinositol-4,5-biphosphate ($PIP_2$) in a process regulated by PKC phosphorylation (Glaser, et al., J. Biol. Chem 271, 26187–93 (1996)). It seems reasonable to propose that $PIP_2$ may also play a key role in the priming of Calcyon-enabled, D1 receptor stimulated $Ca^{++}$ release as M1 and P2Y receptor stimulation results in activation of phospholipase Cβ, an enzyme which converts $PIP_2$ to diacylglycerol (DAG) and $IP_3$. If, like MARCKS, Calcyon sequesters $PIP_2$, one might predict that EGFP-Calcyon expression would inhibit M1 or P2Y-stimulated $Ca^{++}_i$ release. Data shown in FIGS. 3a–3c comparing P2Y and M1 stimulated $Ca^{++}_i$ release in EGFP versus EGFP-Calcyon expressing D1HEK293 cells are consistent with this notion. Reasoning further by analogy to MARCKS, if $G_q$-coupled receptor stimulation leads to additional phosphorylation of Calcyon, the liberated pools of $PIP_2$ may contribute to the large increase in $Ca^{++}$ mobilized by D1 receptor stimulation. Other studies showed that the PKC inhibitor bisindolylmalemide inhibits Calcyon-enabled D1 stimulated $Ca_i^{++}$ release.

Figure 4:
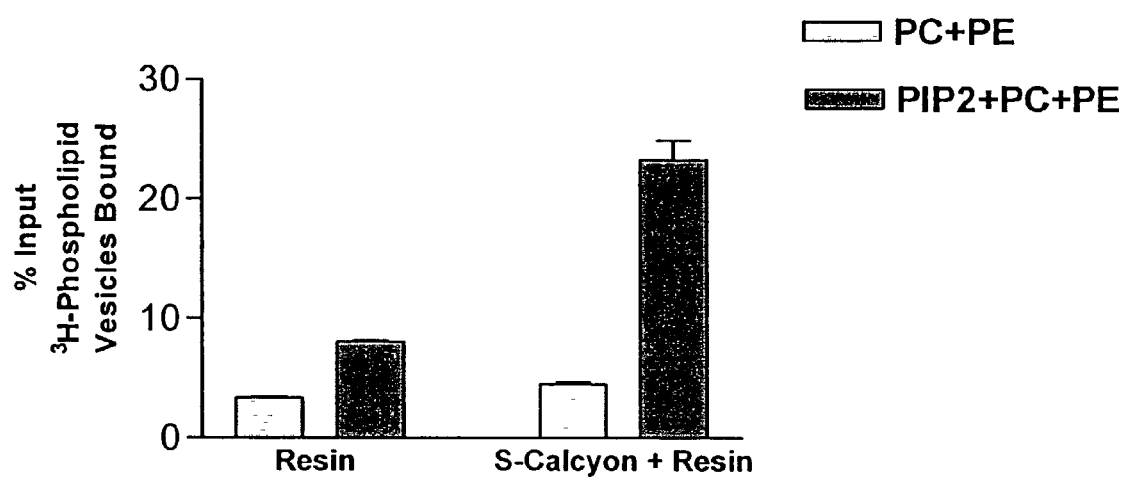
FIG. 4 is a graph showing that calcyon's cytoplasmic domain binds PIP2. S-Calcyon bound to 25 µl of S-agarose resin, or 25 µl of S-agarose resin only was incubated for one hour at room temperature with phospholipid vesicles containing phosphotidylcholine (PC), phosphotidylethanolamine (PE), or PC, PE, and $PIP_2$. Both types of vesicles were radioactively labeled with equivalent amounts of $^3$H-phosphatidylcholine. Following incubation, resins were washed three times with ten volumes of buffer (20 mM hepes, pH 7.4), and amounts of bound phospholipid determined by liquid scintillation counting. Results are reported as percent of input radiolabel precipitated. Bars represent average value obtained in three independent assays with standard error of the mean.

Tests were conducted to determine whether Calcyon can bind $PIP_2$ using the S-Calcyon fusion protein. S-Calcyon contains the predicted cytoplasmic domain of Calcyon (residues 93–217) preceded by an 'S' tag (for coupling to S-agarose resin). S-Calcyon bound to 25 µl of S-agarose resin was incubated for one hour at room temperature with phospholipid vesicles containing phosphotidylcholine (PC), phosphotidylethanolamine (PE), or PC, PE, and $PIP_2$. Both types of vesicles were radioactively labeled with equivalent amounts of $^3H$-phosphatidylcholine. Following incubation, resin was washed three times with ten volumes of buffer (20 mM Hepes, pH 7.4), and amounts of bound phospholipid were determined by liquid scintillation counting. Parallel assays were conducted with 25 µl of S-agarose to control for non-specific binding of phospholipid to resin only. Results are reported as percent of input radiolabel precipitated, bars represent the standard error of the mean of each value determined in triplicate. S-Calcyon bound to resin precipitated $PIP_2$ containing vesicles more than five times more effectively that vesicles composed of PC and PE only (FIG. 4). The presence of $PIP_2$ in lipid vesicle composition makes a significant difference ($p<0.001$) in the ability of S-Calcyon to bind phospholipid. In addition, attachment of S-Calcyon appears to significantly improve S-agarose resin binding to the $PIP_2$ containing vesicles ($p<0.001$). These results are indicative that Calcyon does sequester $PIP_2$, and therefore that EGFP-Calcyon expression would inhibit M1 or P2Y-stimulated $Ca_i^{++}$ release.

Modifications and variations of the methods and materials described herein will be encompassed by the following claims. References cited herein are specifically incorporated.

I claim:

1. An isolated polynucleotide comprising:
   (a) a nucleic acid sequence encoding the calcyon protein of SEQ ID NO: 2; or
   (b) a fragment of the nucleic acid sequence of SEQ ID NO: 1 that encodes a fragment of the protein of SEQ ID NO: 2, wherein said fragment of the protein of SEQ ID NO: 2 is at least 125 amino acids in length.

2. The polynucleotide of claim 1 having the sequence of SEQ ID NO: 1.

3. The isolated polynucleotide of claim 1 having a detectable label attached thereto.

4. The polynucleotide of claim 1 wherein the fragment of SEQ ID NO: 2, comprises amino acids 93 to 217 of SEQ ID NO: 2.

5. The isolated polynucleotide of claim 1, comprising nucleic acids 117 to 767 of SEQ ID NO: 1.

6. An isolated nolynucleotide consisting of at least 14 contiguous nucleotides of nucleic acids 117 to 767 of SEQ ID NO: 1 or the reverse complement of nucleic acids 117 to 767 of SEQ ID NO: 1.

7. An isolated polynucleotide encoding a fragment of the protein of SEQ ID NO: 2, wherein said fragment comprises at least 20 consecutive amino acids of SEQ ID NO: 2.

8. The isolated polynucleotide of claim 7, comprising nucleic acids 279 to 338 of SEQ ID NO: 1 encoding a polypeptide having the sequence of SEQ ID NO: 5.

9. A plurality of isolated polynucleotides, each polynucleotide consisting of at least 14 contiguous nucleotides of the nucleic acid sequence of SEQ ID NO: 1 or the reverse complement of SEQ ID NO: 1, wherein each of the isolated polynucleotides or the reverse complement of each of the isolated polynucleotides do not include any overlapping sequences.

* * * * *

UNITED STATES PATENT AND TRADEMARK OFFICE
CERTIFICATE OF CORRECTION

PATENT NO.        : 7,220,851 B2                                              Page 1 of 1
APPLICATION NO. : 10/237523
DATED             : May 22, 2007
INVENTOR(S)       : Clare Bergson It is certified that error appears in the above-identified patent and that said Letters Patent is hereby corrected as shown below:

Under "BRIEF DESCRIPTION OF THE DRAWING"

Column 3 Line 63, the phrase "BRIEF DESCRIPTION OF THE DRAWING" should read --BRIEF DESCRIPTION OF THE DRAWINGS--

Column 3 Line 66, the phrase "Fig 1. is the nucleotide sequence, SEQ ID NO: 1and" should read --Fig 1. is the nucleotide sequence, SEQ ID NO: 1 and--

Under "DETAILED DESCRIPTION OF THE INVENTION"

Column 5 Line 26, the phrase "multiple arrestin molecules may be required to regulated" should read --multiple arrestin molecules may be required to regulate--

Column 14 Line 9, the phrase "Characterization of P24" should read --Characterization of Calcyon (P24)--

Column 16 Line 53, the phrase "In, addition, the results of these in vitro experiments" should read --In addition, the results of these in vitro experiments--

Signed and Sealed this

Nineteenth Day of August, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 217
<212> TYPE: PRT
<213> ORGANISM: Artificial Sequence
<220> FEATURE:
<223> OTHER INFORMATION: D1-Like dopamine receptor activity modifying
      protein

<400> SEQUENCE: 1

Met Val Lys Leu Gly Cys Ser Phe Ser Gly Lys Pro Gly Lys Asp Pro
1               5                   10                  15

Gly Asp Gln Asp Gly Ala Ala Met Asp Ser Val Pro Leu Ile Ser Pro
            20                  25                  30

Leu Asp Ile Ser Gln Leu Gln Pro Leu Pro Asp Gln Val Val Ile
        35                  40                  45

Lys Thr Gln Thr Glu Tyr Gln Leu Ser Ser Pro Asp Gln Gln Asn Phe
    50                  55                  60

Pro Asp Leu Glu Gly Gln Arg Leu Asn Cys Ser His Pro Glu Glu Gly
65                  70                  75                  80

Arg Arg Leu Pro Thr Ala Arg Met Ile Ala Phe Ala Met Ala Leu Leu
            85                  90                  95

Gly Cys Val Leu Ile Met Tyr Lys Ala Ile Trp Tyr Asp Gln Phe Thr
            100                 105                 110

Cys Pro Asp Gly Phe Leu Leu Arg His Lys Ile Cys Thr Pro Leu Thr
            115                 120                 125

Leu Glu Met Tyr Tyr Thr Glu Met Asp Pro Glu Arg His Arg Ser Ile
    130                 135                 140

Leu Ala Ala Ile Gly Ala Tyr Pro Leu Ser Arg Lys His Gly Thr Glu
145                 150                 155                 160

Thr Pro Ala Ala Trp Gly Asp Gly Tyr Arg Ala Ala Lys Glu Glu Arg
            165                 170                 175

Lys Gly Pro Thr Gln Ala Gly Ala Ala Ala Ala Thr Glu Pro Pro
            180                 185                 190

Gly Lys Pro Ser Ala Lys Ala Glu Lys Glu Ala Ala Arg Lys Ala Ala
            195                 200                 205

```
Gly Ser Ala Ala Pro Pro Ala Gln
    210             215
```

```
<210> SEQ ID NO 2
<211> LENGTH: 936
<212> TYPE: DNA
<213> ORGANISM: Artificial Sequence
<220> FEATURE:
<223> OTHER INFORMATION: D1-Like dopamine receptor activity modifying
      protein

<400> SEQUENCE: 2
gaattcgcgg ccgcgtcgac cgcatcctcc gcatccacat ccgcatcgtc gtcctccccg     60
accgcgtcct gcagcagctg ccagtggagc cgcctgacaa gggactgcca tccaccatgg    120
tgaagctggg ctgcagcttc tctgggaagc caggtaaaga ccctggggac caggatgggg    180
ctgccatgga cagtgtgcct ctgatcagcc ccttggacat cagccagctc cagccgccac    240
tccctgacca ggtggtcatc aagacacaga cagaatacca gctgtcctcc ccagaccagc    300
agaatttccc tgacctggag ggccagaggc tgaactgcag ccacccagag aagggcgca    360 ggctgcccac cgcacggatg atcgccttcg ccatggcgct actgggctgc gtgctgatca    420
tgtacaaggc catctggtac gaccagttca cctgccccga cggcttcctg ctgcggcaca    480
agatctgcac gccgctgacc ctggagatgt actacacgga gatggacccc gagcgccacc    540
gcagcatcct ggcggccatc ggggcctacc gctgagccg caagcacggc acggagacgc    600
cggcggcctg gggggacggc taccgcgcag ccaaggagga gcgcaagggg cccacccagg    660
ctggggcggc ggcggcggcc accgaacccc ccgggaagcc gtcggccaag gcggagaagg    720
aggcggcgcg gaaggcggcc gggagcgcgg cgccccgcc cgcgcagtga cgtctccagc    780
cccgcagccc ggcccgggcg tcctccgcca gctcctgtga ccagcgcgtc tcccgatgct    840
ctccgccgtg ttcgtgtccc caggcgccct cgctgcagcc cgccccgt gggtctctga     900 ctctgtcgct tttctctaag taaagatttc acgtcc                              936
```

```
<210> SEQ ID NO 3
<211> LENGTH: 15
<212> TYPE: PRT
<213> ORGANISM: Homo sapiens

<400> SEQUENCE: 3

Ser Val Ile Leu Asp Tyr Asp Thr Asp Val Ser Leu Glu Lys Ile
1               5                   10                  15
```

```
<210> SEQ ID NO 4
<211> LENGTH: 17
<212> TYPE: PRT
<213> ORGANISM: Homo sapiens

<400> SEQUENCE: 4

Asn Glu Asp Gln Lys Ile Gly Ile Glu Ile Ile Lys Arg Ala Leu Lys
1               5                   10                  15

Ile
```

```
<210> SEQ ID NO 5
<211> LENGTH: 20
<212> TYPE: PRT
<213> ORGANISM: Homo sapiens

<400> SEQUENCE: 5

Gln Leu Ser Ser Pro Asp Gln Gln Asn Phe Pro Asp Leu Glu Gly Gln
```

```
1               5               10              15
Arg Leu Asn Cys
            20
```